(12) United States Patent
Barr et al.

(10) Patent No.: US 7,914,771 B2
(45) Date of Patent: Mar. 29, 2011

(54) TREATMENT OF CHRONIC OBSTRUCTIVE PULMONARY DISEASE BY LOW DOSE INHALATION OF PROTEASE INHIBITOR

(75) Inventors: Philip J. Barr, Oakland, CA (US); Philip A. Pemberton, San Mateo, CA (US); Helen L. Gibson, Oakland, CA (US)

(73) Assignee: Arriva Pharmaceuticals, Inc., Alameda, CA (US)

( * ) Notice: Subject to any disclaimer, the term of this patent is extended or adjusted under 35 U.S.C. 154(b) by 420 days.

(21) Appl. No.: 11/077,276

(22) Filed: Mar. 9, 2005

(65) Prior Publication Data

US 2005/0201951 A1    Sep. 15, 2005

Related U.S. Application Data

(60) Provisional application No. 60/551,856, filed on Mar. 9, 2004.

(51) Int. Cl.
*A61K 38/55* (2006.01)
*A61K 9/14* (2006.01)

(52) U.S. Cl. ............... 424/46; 424/9.1; 514/2; 514/12

(58) Field of Classification Search ............ 424/46, 424/9.1; 514/12, 2
See application file for complete search history.

(56) References Cited

U.S. PATENT DOCUMENTS

| | | | |
|---|---|---|---|
| 4,732,973 A | 3/1988 | Barr et al. | |
| 4,752,576 A | 6/1988 | Brake et al. | |
| 4,837,148 A | 6/1989 | Cregg | |
| 4,870,008 A | 9/1989 | Brake | |
| 5,008,242 A | 4/1991 | Lezdey et al. | |
| 5,093,316 A | 3/1992 | Lezdey et al. | |
| 5,114,953 A | 5/1992 | Galardy et al. | |
| 5,134,119 A | 7/1992 | Lezdey et al. | |
| 5,166,134 A | 11/1992 | Lezdey et al. | |
| 5,217,951 A | 6/1993 | Lezdey et al. | |
| 5,256,657 A | 10/1993 | Singh et al. | |
| 5,290,762 A | 3/1994 | Lezdey et al. | |
| 5,594,106 A | 1/1997 | Black et al. | |
| 5,618,786 A | 4/1997 | Roosdorp et al. | |
| 5,696,147 A | 12/1997 | Galardy | |
| 5,773,438 A | 6/1998 | Levy et al. | |
| 5,780,440 A | 7/1998 | Lezdey et al. | |
| 5,892,112 A | 4/1999 | Levy et al. | |
| 5,972,986 A | 10/1999 | Seibert et al. | |
| 5,993,783 A | 11/1999 | Eljamal et al. | |
| 6,068,994 A | 5/2000 | Barr et al. | |
| 6,124,257 A | 9/2000 | Lezdey et al. | |
| 6,133,304 A | 10/2000 | Peterson, Jr. et al. | |
| RE37,053 E | 2/2001 | Hanes et al. | |
| 6,469,040 B2 | 10/2002 | Seibert et al. | |
| 6,489,308 B1 | 12/2002 | Shapiro et al. | |
| 6,544,497 B2 | 4/2003 | Zhu et al. | |
| 6,693,096 B2 | 2/2004 | Fritz et al. | |
| 6,740,655 B2 | 5/2004 | Magee et al. | |
| 7,247,704 B2 * | 7/2007 | Barr et al. ............... 530/350 |
| 2001/0006939 A1 | 7/2001 | Niven et al. | |
| 2002/0099013 A1 | 7/2002 | Piccariello et al. | |
| 2003/0068280 A1 | 4/2003 | Bannister et al. | |
| 2003/0073217 A1 | 4/2003 | Barr et al. | |
| 2003/0078276 A1 | 4/2003 | Andrianjara et al. | |
| 2003/0211548 A1 | 11/2003 | Packard et al. | |
| 2005/0201951 A1 * | 9/2005 | Barr et al. ............ 424/46 |
| 2008/0312136 A1 * | 12/2008 | Durrani et al. .......... 514/8 |

FOREIGN PATENT DOCUMENTS

| | | |
|---|---|---|
| EP | 0 648 838 B1 | 4/1995 |
| EP | 1 226 119 B1 | 7/2002 |
| EP | 1 226 136 B1 | 7/2002 |
| EP | 1 047 450 B1 | 10/2002 |
| WO | WO 92/09282 | 6/1992 |
| WO | WO 92/09556 | 6/1992 |
| WO | WO 92/09563 | 6/1992 |
| WO | WO 93/13741 | 7/1993 |
| WO | WO 94/02446 | 2/1994 |
| WO | WO 94/21625 | 9/1994 |
| WO | WO 94/22309 | 10/1994 |
| WO | WO 95/09841 | 4/1995 |
| WO | WO 95/19965 | 7/1995 |
| WO | WO 96/16027 | 5/1996 |
| WO | WO 96/32152 | 10/1996 |
| WO | WO 97/42168 | 11/1997 |
| WO | WO 98/07742 | 2/1998 |
| WO | WO 98/14424 | 4/1998 |
| WO | WO 98/43946 | 10/1998 |
| WO | WO 98/47863 | 10/1998 |
| WO | WO 99/32150 | 7/1999 |
| WO | WO 99/44989 | 9/1999 |
| WO | WO 00/34237 | 6/2000 |
| WO | WO 02/50287 | 6/2002 |

(Continued)

OTHER PUBLICATIONS

Barnes, Peter J., "Novel Approaches and Targets for Treatment of Chronic Obstructive Pulmonary Disease", Am. J. Respir. Crit. Care Med. vol. 160, pp. S72-S79, 1999.

Travis, James et al., "Isolation and Properties of Recombinant DNA Produced Variants of Human Proteinase Inhibitor", The Journal of Biological Chemistry, vol. 260, No. 7, Issue of Apr. 10, pp. 4384-4389, 1985.

Roche, N. et al., "Current issues in the management of chronic obstructive pulmonary diseases", Respirology, vol. 2, pp. 215-229, 1997.

He, J.Q. et al., "Pharnacogenomics of COPD", Current Pharmacogenomics, pp. 229-243, 2003.

Churg et al., "Proteases and Emphysema", Current Opinion in Pulmonary Medicine 11:153-159 (2005).

Huang et al., "Expression and Purification of Functional Human $a_1$-Antitrypsin from Cultured Plant Cells", Biotechnol Prog. 17, 126-33 (2001).

(Continued)

*Primary Examiner* — Chih-Min Kam
(74) *Attorney, Agent, or Firm* — Arnold and Porter LLP; Jeffrey P. Bernhardt

(57) ABSTRACT

The present invention encompasses methods and compositions for the treatment and prevention of chronic obstructive pulmonary disease (COPD) or emphysema, typically smoking-induced emphysema. More specifically, the present invention relates to the treatment and prevention of COPD or emphysema by inhalation of alpha one-antitrypsin (AAT).

14 Claims, No Drawings

FOREIGN PATENT DOCUMENTS

| | | |
|---|---|---|
| WO | WO 02/053138 A2 | 7/2002 |
| WO | WO 02/064080 | 8/2002 |
| WO | WO 03/068188 A1 | 8/2003 |
| WO | WO 03/075959 | 9/2003 |
| WO | WO 2004/103364 | 12/2004 |
| WO | WO 2005/003150 A2 | 1/2005 |

OTHER PUBLICATIONS

Rabe, "Outcome Measures in COPD", Primary Care Respiratory Journal, 13:177-178 (2004).
Rosenerg et al., "Synthesis in Yeast of a Functional Oxidation-Resistant Mutant of Human $a_1$-Antitrypsin", Nature vol. 312, pp. 77-80, (1984).
Shapiro, "Envolving Concepts in the Pathogenesis of Chronic Obstructive Pulmonary Disease", Clinics in Chest Medicine, vol. 21, No. 4, pp. 621-632, (2000).
Travis et al., "Isolation and Properties of Recombinant DNA Produced Variants of Human $a_1$-Proteinase Inhibitor", Journal of Biological Chemistry, vol. 260, No. 7, pp. 4384-4389, (1985).
Terashima et al., "Production of Functional Human $a_1$-Antitrypsin by Plant Cell Culture", Appl. Microbiol Biotechnol, 52:516-23 (1999).
Beatty, K., et al., "Kinetics of association of serine proteinases with native and oxidized alpha-1-proteinase inhibitor and alpha-1-antichymotrypsin," *J. Biol. Chem.*—255(9):3931-3934 (1980).
Carrell, R.W., et al., "Structure and variation of human alpha 1-antitrypsin", *Nature*—298:329-334 (1982).
Hercz, A., "Proteolytic cleavages in alpha-one antitrypsin and microheterogeneity," *Biochem. Biophys. Res. Comm.*—128(1): 199-203 (1985).
Schasteen, C.S., et al., "Synthetic peptide inhibitors of complement serine proteases—III. Significant increase in inhibitor potency provides further support for the functional equivalence hypothesis," *Mol. Immunol.* 28(1/2):17-26 (1991).
Stolk, et al., "Progression parameters for emphysema: A clinical investigation," *Respiratory Medicine.*—(101) 1924-1930 (2007).
Stockley, et al., "Therapeutic efficacy of alpha-1 antitrypsin (AAT) augmentation therapy on the loss of lung tissue: an integrated analysis", *European Respiratory Society*—(Abstract) Oct. 7, 2008.
Pemberton, Philip A., et al., "Inhaled Recombinant Alpha 1-Antitrypsin Ameliorates Cigarette Smoke-Induced Emphysema in the Mouse", COPD:Journal of Chronic Obstructive Pulmonary Disease, 3:101-108, 2006.
Barnes, P. J., "Chronic Obstructive Pulmonary Disease," The New England Journal of Medicine, 343(4): 269-280, 2000.
Barnes, P. J., "Mechanisms in COPD; Differences From Asthma," Chest, 117(2): I0S-14S, 2000.
Barnes, P.J., "Novel Approaches and Targets for Treatment of Chronic Obstructive Pulmonary Disease," American Journal of Respiratory and Critical Care Medicine, 160(5): S72-S79, 1999.
Bingle L. et al., "Susceptibility of Lung Epithelium to Neutrophil Elastase: Protection by Native Inhibitors," Mediators of Inflammation, 6:345-354, 1997.
Bingle, et al., "Secretory leukoprotease inhibitor: Partnering $α_1$-proteinase inhibitor to combat pulmonary inflammation," 51: 1273-1274, 1996.
Bode, W., et al., "Proteinase-Protein Inhibitor Interactions," Fibrinolysis, 8(1): 161-171, 1994.
Levels on the Respiratory Epithelial Surface by Aerosolization of Recombinant Secretory Leukoprotease Inhibitor, The J. of Clin. Inves., 90: 1296-1301, 1992.
Okayama, H., et al., "Characterization of the Coding Sequence of the Normal M4 $α_1$-Antitrypsin Gene," Biochem. Biophys. Res. Commun., 162(3): 1560-1570, 1989.
Okayama, H., et al., Am. J. Hum. Genet., 48(6): 1154-1158, 1991.
Patterson, S.D., "Mammalian $α_1$-Antitrypsins: Comparative Biochemistry and Genetics of the Major Plasma Serpin," Comp Biochem. Physiol., 100B(3):439-454, 1991.
Potempa, J., et al., "The Serpin Superfamily of Proteinase Inhibitors: Structure, Function, and Regulation," The J. of Biol. Chem., 269(23): 15957-15960,1994.
Prouty, R., Office Action in U.S. Appl. No. 11/781,152 mailed Nov. 13, 2008.

Rudolphus, A., et al., "Intratracheally-Instilled antileukoprotease and $α1$-Proteinase Inhibitor: Effect on Human Neutrophil Elastase-Induced Experimental Emphysema and Pulmonary Localization," Histochemical Journal, 26: 817-824, 1994.
Salahuddin, P., "Alpha-1-Antitrypsin-Structure, Function and Genetic Variants," Indian J. Biochem. & Biophys, 28: 164-167, 1991.
Schasteen, C.S., et al., Molecular Immunology, 28(1/2): 472-479, 1991.
Sesboue R., et al., "Human Alpha1-Antitrypsin Genetic Polymorphism: PI N Subtypes," Hum. Hered, 34: 105-113, 1984.
Silverman, G.A., et al., "The Serpins are an Expanding Superfamily of Structurally Similar but Functionally Diverse Proteins," The Journal of Biological Chemistry, 276(36): 33293-33296, 2001.
Smith, et al., "Pulmonary Deposition and Clearance of Aerosolized Alpha-1-Proteinase Inhibitor Administered to Dogs and to Sheep," J. Clin. Invest., 84: 1145-1154, 1989.
Swope, S., Final Office Action in U.S. Appl. No. 10/578,692 mailed Mar. 4, 2009.
Swope, S., Office Action in U.S. Appl. No. 10/578,692 mailed Apr. 10, 2008.
Tamer, M., et al., "Production and Recovery of Recombinant Protease Inhibitor Alpha1-Antitrypsin," Enzyme and Microbial Technology, 29: 611-620, 2001.
Wright, C.D., et al., "Secretory Leukocyte Protease Inhibitor Prevents Allergen-Induced Pulmonary Responses in Animal Models of Asthma," The Journal of Pharmacology and Experimental Therapeutics, 289(2): 1007-1014, 1999.
Hubbard, R.C., et al., "Anti-Neutrophil-Elastase Defenses of the Lower Respiratory Tract in Alpha 1-Antitrypsin Deficiency Directly Augmented with an Aerosol of Alpha 1-Antitrypsin," Annals of Internal Medicine, 111(3): 206-212, 1989.
He, J.Q., et al., "Pharmacogenomics of COPD,"Current Pharmacogenomics, 1(4): 229-243, 2003.
Brantly, M.L., et al., "Use of a Highly Purified $α_1$-Antitrypsin Standard to Establish Ranges for the Common Normal and Deficient $α_1$-Antitrypsin Phenotypes," Chest, 100(3): 703-708, 1991.
Carrell, R.W., et al., "Reduction in the Incidence of Type 2 Diabetes with Lifestyle Intervention or Metformin," N. Engl. J. Med., 346: 45-53, 2002.
Chughtai, B., et al., "Potential Role of Inhibitors of Neutrophil Elastase in Treating Diseases of the Airway," Journal of Aerosol Medicine, 17(4): 289-298, 2004.
Cox, D.W., et al., "Three New Rare Variants of $α_1$-Antitrypsin," Hum. Genet., 61(1): 123-126, 1982.
Crystal, R.G. et al., "The $α_1$-Antitrypsin Gene and Its Mutations, Clinical Consequences and Strategies for Therapy," Chest, 95(1): 196-208, 1989.
Curiel, D., et al., "Characterization of the Sequence of the Normal $α_1$-Antitrypsin M3 Allele and Function of the M3 Protein," Am. J. Respir. Cell Mol. Biol., 1:471-477, 1989.
Dykes, D.D., et al., "Distribution of $α_1$-Antitrypsin Variants in a US White Population," Hum. Hered, 34(5): 308-310, 1984.
Dykes, D.D., et al., "Review of Isoelectri Focusing for Gc, PGM, Tf, and Pi Subtypes: Population Distributions," CRC Crit. Rev. Clin. Lab Sci., 20(2): 115-151, 1984.
Edwards, D.A., et al., "Large Porous Particles for Pulmonary Drug Delivery," Science, 276: 1868-1871, 1997.
Faber, J.P., et al., "Identification and DNA Sequence Analysis of 15 New $α_1$-Antitrypsin Variants, Including Two Pl*Q0 Alleles and One Deficient Pl*M Allele," Am. J. Hum. Genet., 55: 1113-1121, 1994.
Gadek, et al., "$α_1$-Antitrypsin Deficiency," The Metabolic Basis of Inherited Diesease, Stanbury, J.B. et al., eds., McGraw-Hill, New York, pp. 1450-1467, 1982.
Gahne, B., et al., "Extensive Genetic Polymorphism of Four Plasma $α$-protease Inhibitors in Pigs and Evidence for Tight Linkage Between the Structural Loci of these Inhibitors," Anim. Genet., 17(2): 135-157, 1986.
GenBank Accession No. AAB59375, $α_1$-Antitrypsin, (Nov. 1994).
Hunnighake, G.W., et al., "Cigarette Smoking and Lung Destruction: Accumulation of Neutrophils in the Lungs of Cigarette Smokers," Am. Rev. Respir. Dis., 128: 833-838, 1983.

Jeppsson, J.O., et al., "The Amino Acid Substitutions of Human $\alpha_1$-Antitrypsin $M_3$, X and Z," FEBS Let., 231(2): 327-330, 1998.

Kurachi, K., et al., "Cloning and Sequence of cDNA Coding for $\alpha_1$-Antitrypsin," Proc Natl Acad Sci USA, Biochemistry, 78(11): 6826-6830, 1981.

McElvaney, N. G. et al., Modulation of Airway Inflammation in Cystic Fibrosis: In Vivo Suppression of Interleukin-8.

* cited by examiner

TREATMENT OF CHRONIC OBSTRUCTIVE PULMONARY DISEASE BY LOW DOSE INHALATION OF PROTEASE INHIBITOR

CROSS-REFERENCE TO RELATED APPLICATIONS

This application claims the benefit of U.S. provisional patent application No. 60/551,856, filed Mar. 9, 2004, the disclosure of which is incorporated herein by reference in its entirety.

BACKGROUND OF THE INVENTION

Chronic obstructive pulmonary disease ("COPD") is a disease state characterized by airflow limitation that is not fully reversible, and that is usually both progressive and associated with an abnormal inflammatory response of the lungs to noxious particles or gas. Global Initiative for Chronic Obstructive Lung Disease Workshop Report (2004) ("Gold Report").

COPD is the fourth leading cause of chronic morbidity and mortality in the United States, Gold Report, and is the fifth leading cause of death in the world, Rabe, "Outcome measures in COPD," Primary Care Respiratory J. 13:177-178 (2004); World Health Organization, World Health Report 2002.

In 1993, the 15.7 million cases of COPD in the United States were estimated to present an annual economic burden of $23.9 billion; in the United Kingdom, the direct cost of COPD in 1996 was approximately $1.4 billion, with indirect costs estimated at approximately $3.4 billion. Gold Report 2004. Worldwide, prevalence is increasing, and by 2020 COPD is projected to rank fifth in terms of worldwide disease burden.

Currently, treatment of COPD is largely palliative; none of the existing approaches clearly halts progression of the disease.

Typically, the clinical manifestations of COPD are associated with histopathologic evidence of emphysema, defined as destruction of the alveoli. Cigarette smoke-induced emphysema is a principal contributor to the pathogenesis of COPD.

Smoke-induced emphysema is presumed to result, at least in part, from an imbalance between protease and antiprotease activity in the lungs.

Individuals with hereditary deficiency of alpha 1-antitrypsin (AAT), a major inhibitor of neutrophil elastase, are known to develop panacinar emphysema, even in the absence of smoke exposure. Cigarette smoke is known to oxidatively inactivate alpha 1-antitrypsin (AAT), and smoke exposure is known to cause an increase in the numbers of protease-secreting inflammatory cells, including neutrophils, in the lungs, causing an analogous protease-antiprotease imbalance in the lungs of individuals without hereditary AAT deficiency. Reviewed in Churg et al., Curr. Opin. Pulm. Med. 11:153-159 (2005).

Mice lacking neutrophil elastase (NE) are approximately 60% protected against smoke-induced emphysema, Shapiro, Clin. Chest Med. 21:621-632 (2000). Conversely, peritoneal administration of AAT to NE$^+$ mice provides partial protection from smoke-induced emphysema, reducing airspace size by 63% as compared with the smoke-exposed animals, with concomitant decrease in TNF-α. Churg et al., Am. J. Respir. Crit. Care Med. 168:199-207 (2003).

These, and similar results, have led over the years to periodic suggestions that smoke-induced emphysema and COPD (of any etiology) be treated by AAT supplementation. U.S. Pat. No. 5,093,316, for example, describes and claims a method for treating the symptoms of pulmonary diseases, including COPD, by administering an effective amount of microcrystalline alpha 1-antitrypsin by inhalation. U.S. Pat. No. 6,489,308 proposes to treat a variety of disorders, including COPD, by administration of AAT. U.S. Pat. No. 5,993,783 describes a formulation of AAT intended for dry powder delivery to the lungs of patients having certain types of emphysema.

Native human AAT derived from pooled human plasma is commercially available and approved for intravenous administration to patients having hereditary deficiency of alpha 1-antitrypsin. The presence of copurifying protein contaminants and the risk of transmitting infectious agents militates against more widespread use, however, and has motivated the development of recombinant AAT and engineered AAT muteins. Recombinant AAT has been produced, for example, in yeast, Rosenberg et al., Nature 312:77-80 (1984); U.S. Pat. No. 4,752,576; Travis et al., J. Biol. Chem. 260:4384-4389 (1985); and in plants, Terashima et al., Appl. Microbiol. Biotechnol. 52:516-23 (1999) and Huang et al., Biotechnol. Prog. 17:126-33 (2001).

One type of recombinant AAT produced in Saccharomyces cerevisiae, rAAT, has an amino acid sequence identical to human plasma AAT with the exception of an N-acetylmethionine residue at the amino terminus. Unlike native human AAT, rAAT is unglycosylated.

Although production of rAAT in yeast provides certain advantages in terms of yield, cost, and ease of purification, the unglycosylated yeast-derived rAAT is considerably less tolerant of heat than its natural glycosylated counterpart. Travis et al., J. Biol. Chem. 260:4384-4389 (1985). Unglycosylated rAAT also has a far shorter biological half life.

Despite the partial protection from smoke-induced emphysema afforded by intraperitoneal supplementation with glycosylated human AAT in mice, and despite the various suggestions that AAT be delivered by inhalation to patients suffering from or at risk for COPD, the ability to achieve protective levels of antiprotease by inhalation of an unglycosylated recombinant protein in the concurrent presence of oxidizing cigarette smoke cannot be predicted. Furthermore, native AAT is inactivated by matrix metalloproteases, which are often elevated in the lungs of smokers; the ability to achieve protective levels of antiprotease by inhalation of an unglycosylated recombinant AAT in the concurrent presence of matrix metalloproteases cannot be predicted. In particular, it cannot be predicted whether pulmonary administration can provide protective levels of antiprotease activity in the lung interstitium at risk for protease degradation in smokers.

There still exists a need for effective methods of treating smoking-induced emphysema and COPD. There exists, in particular, a continuing need for treatments that can halt or retard progression in airflow limitation in individuals having, or at risk for, smoke-induced emphysema and COPD. There exists a further need for therapeutic methods that do not rely upon administration of agents derived from human plasma.

SUMMARY OF THE INVENTION

The present invention solves these and other needs in the art by providing, in a first aspect, methods of treating chronic obstructive pulmonary disease (COPD).

The methods comprise administering an effective amount of alpha 1-antitrypsin (AAT), typically unglycosylated AAT, or functionally active portion thereof, by inhalation to the lungs of an individual having or at risk of developing COPD.

In various embodiments, the lungs of the treated individual are periodically exposed to at least one airborne agent capable of oxidizing AAT, such as tobacco smoke. In some of these embodiments, the individual being treated is a smoker.

In certain embodiments, the unglycosylated AAT is recombinant AAT, such as rAAT, expressed in yeast.

In one series of embodiments, the unglycosylated AAT, or functionally active portion thereof, is administered as a dry powder composition.

In certain of these embodiments, the dry powder composition comprises AAT or functionally active portion thereof and a halide salt. The halide salt is present, in some embodiments, at a level of at least about 10 micromoles per 100 mg AAT. In various embodiments, the halide salt is present at a level of at least about 50 micromoles per 100 mg AAT. In certain embodiments, the halide salt is present at a level of at least about 100 micromoles per 100 mg AAT. Typically, the halide salt is a chloride salt, such as NaCl.

The dry powder composition, in some embodiments, is substantially free of carbohydrate.

In another series of embodiments, the unglycosylated AAT, or functionally active portion thereof, is administered as a liquid composition, for example as an aerosol.

In some of these embodiments, the liquid composition is rehydrated from a dry composition comprising unglycosylated AAT, or functionally active portion thereof, and a halide salt. The halide salt is present, in some embodiments, at a level of at least about 10 micromoles per 100 mg AAT. In various embodiments, the halide salt is present at a level of at least about 50 micromoles per 100 mg AAT. In certain embodiments, the halide salt is present at a level of at least about 100 micromoles per 100 mg AAT. Typically, the halide salt is a chloride salt, such as NaCl.

In certain of these embodiments, the AAT is rAAT or a functionally active portion thereof.

The dry composition from which the administrable liquid is rehydrated is, in certain embodiments, substantially free of carbohydrate.

In various embodiments of the methods of the present invention, no more than about 200 mg of unglycosylated AAT, or functionally active portion thereof, is administered per day. In some embodiments, no more than about 100 mg of unglycosylated AAT, or functionally active portion thereof, is administered per day. In others, no more than about 50 mg of unglycosylated AAT, or functionally active portion thereof, is administered per day.

In a variety of embodiments of the methods of the present invention, no more than about 100 mg unglycosylated AAT or functionally active portion thereof is administered in any single dose. In some embodiments, no more than about 50 mg unglycosylated AAT or functionally active portion thereof is administered in any single dose, even no more than about 25 mg unglycosylated AAT or functionally active portion thereof is administered in any single dose. In some embodiments, no more than about 20 mg unglycosylated AAT or functionally active portion thereof is administered in any single dose.

In certain embodiments, the method further comprises administering an effective amount of at least a second protease inhibitor, or functionally active portion thereof, by inhalation.

The second protease inhibitor can, for example, be an inhibitor of at least one matrix metalloprotease. The second protease inhibitor can, for example, be selected from the group consisting of TIMP-1, TIMP-2, TIMP-3, TIMP-4, and ilomastat, and is usefully TIMP-1 or functionally active portion thereof.

The methods of the present invention may further comprise administering an effective amount of a bronchodilator or corticosteroid by inhalation.

In another aspect, the invention provides a kit for treating COPD.

The kit comprises a device for delivering a therapeutically active agent by inhalation; and at least one dose of unglycosylated AAT or functionally active portion thereof.

In some embodiments, the delivery device is a nebulizer. In certain of these embodiments, the at least one dose of AAT is a dry composition and the kit further comprises a sterile diluent.

In other embodiments, the delivery device is a dry powder inhaler. In yet other embodiments, the delivery device is a metered dose inhaler.

In a further aspect, the invention provides a cigarette comprising tobacco, and unglycosylated AAT.

The unglycosylated AAT can be present within a mouth-proximal filter of the cigarette or may be admixed with the tobacco.

DETAILED DESCRIPTION

In a first aspect, the invention provides a method of treating chronic obstructive pulmonary disease ("COPD").

The method comprises administering an effective amount of alpha 1-antitrypsin (AAT), or functionally active portion thereof, by inhalation to the lungs of an individual having or at risk of developing COPD.

By "treating" is intended all clinically-indicated or clinically-acceptable interventions, in both current smokers ("smokers") and former smokers, including but not limited to: prophylaxis against the development of, or the progression of, clinical and/or histological and/or biochemical and/or pathological indicia (including both symptoms and signs) of COPD; prophylaxis against the development of or the progression of clinical and/or histological and/or biochemical and/or pathological sequelae of COPD, including both short and long-term sequelae; treatment of clinical symptoms of COPD; treatment of clinical and/or histological and/or biochemical and/or pathological signs of COPD; clinical management of the disorder; and palliation.

In certain embodiments, for example, the method effects prophylaxis against the development of, or the progression of, clinical and/or histological and/or biochemical and/or pathological indicia (including both symptoms and signs) of COPD in a current smoker, and is thus a prophylaxis against both the effects of the next smoke exposure and against ongoing, progressive effects of past exposure. In other embodiments, the method effects prophylaxis against the development of, or the progression of, clinical and/or histological and/or biochemical and/or pathological indicia (including both symptoms and signs) of COPD in a former smoker, and is thus prophylaxis against the ongoing, progressive effects caused by past exposure.

In certain embodiments, for example, the method effects prophylaxis against the development of or the progression of clinical and/or histological and/or biochemical and/or pathological sequelae of COPD, including both short and long-term sequelae, in a current smoker, and is thus a prophylaxis against both the effects of the next smoke exposure and against ongoing, progressive effects of past exposure. In other embodiments, the method effects prophylaxis against the development of or the progression of clinical and/or histological and/or biochemical and/or pathological sequelae of COPD, including both short and long-term sequelae, in a former smoker, and is thus a prophylaxis against the ongoing, progressive effects caused by past exposure.

In certain exemplary embodiments, the method effects treatment of clinical symptoms of COPD, either in a current smoker or former smoker.

Further by way of nonlimiting example, the method of the present invention is thus effective to "treat" COPD in either a smoker or former smoker if it is sufficient to prophylax against the development of, or the progression of, airflow limitation, which may, for example, be measured by spirometry. For example, the method is effective to treat COPD in a smoker or former smoker if it is sufficient to prophylax against decreases in, or progressive decrease in, $FEV_1$ (forced expiratory volume in one second). Further by way of nonlimiting example, the method is effective to treat COPD in a smoker or former smoker if it is sufficient to prophylax against decreases in, or progressive decrease in, FVC (forced vital capacity). As another example, the method is effective to treat COPD in a smoker or former smoker if it is sufficient to prophylax against decreases in, or progressive decrease in, the ratio of $FEV_1/FVC$.

As one example, the method is effective to treat COPD in a smoker or former smoker if it is sufficient to prophylax against decreases in, or progressive decrease in, the ratio of $FEV_1/FVC$ below 70%, the minimum expected value in normal adults. As yet another example, the method of the present invention is effective to treat COPD in a smoker or a former smoker if it is sufficient to prophylax against decreases in, or progressive decrease in, arterial $PaO_2$. The method of the present invention is also effective to treat COPD if, for example, it is sufficient to prophylax against increases in, or progressive increase in, $PaCO_2$ in either a current smoker or, in other embodiments, a former smoker. The method of the present invention is also effective to treat COPD, for example, if it is sufficient to prophylax against increases in, or progressive increase in, the usage of supplemental $O_2$ in either a smoker or, in alternative embodiments, a former smoker.

The method of the present invention is also effective to treat if, in addition or in the alternative, it is effective—in a smoker or, in other embodiments, former smoker—to prophylax against the development of, or the progression of, clinical symptoms of COPD, such as dyspnea upon exercise, or reduction in exercise tolerance, chronic cough, whether measured as frequency or as duration of cough, excessive sputum production, or acute bronchitis.

The method of the present invention is also effective to treat COPD if, in addition or in the alternative, it is effective to prophylax against the need for, or the increased usage of, bronchodilators and/or pulmonary or oral corticosteroids, such as oral prednisolone, in either a current smoker or a former smoker.

Also by way of example, the method of the present invention is effective to treat COPD if it is sufficient, in a smoker or a former smoker, to prophylax against the development of, or the progression of, emphysema or goblet cell proliferation in the lungs.

Further by way of example, the method of the present invention is effective to treat COPD if it improves airflow, measured as either $FEV_1$, FVC, or the ratio of $FEV_1/FVC$, improves oxygenation, measured, for example, as increased $PaO_2$, improves $CO_2$ elimination, measured as decreases in $PaCO_2$, reduces dyspnea, either at rest, upon exercise, or upon supervening respiratory infection, or reduces the usage of supplemental $O_2$, either in a smoker or, in other embodiments, a former smoker.

The method is, by way of yet further example, effective to treat COPD if it is sufficient to reduce the number or density of lung goblet cells, either focally or globally, within the lungs of a smoker or former smoker.

The method of the present invention is effective to treat COPD if it is sufficient, for example, to reduce—in a smoker or, in alternative embodiments, a former smoker—the frequency of acute exacerbations of COPD, as assessed either by clinical measures, such as spirometry, or by clinical symptoms, such as dyspnea, cough, or sputum production.

The method of the present invention is also effective to treat COPD if, by way of example, it is sufficient to reduce the frequency of lower respiratory infection in a smoker or a former smoker.

Further by way of nonlimiting example, the method of the present invention is effective to treat COPD if, in either current or former smokers, it improves quality of life measures, such as physical functioning, bodily pain, general health, vitality, social functioning, decreasing the dose of other medications, e.g. palliative care medications or other medications, required to treat the disease, delaying the progression of the disease, decreasing time required for resolution of secondary infection and/or symptoms, and/or prolonging survival of patients.

Alpha 1-antitrypsin (AAT) used in the methods of the present invention is typically human AAT.

Human AAT embodiments include, for example, proteins having serine protease inhibitory activity and the sequence of the human M1V AAT allele, the human M1A AAT allele, the human M2 AAT allele, the human M3 allele, and other naturally-occurring human AAT alleles, either with, or in certain embodiments without, the N-terminal signal sequence. In some embodiments, the human AAT has the sequence shown in U.S. patent application publication no. 2003/0073217, the disclosure of which is incorporated herein by reference in its entirety. In some embodiments, the human AAT has the sequence set forth in Carrell et al., *Nature* 298:329-334 (1982).

In other embodiments, human AAT is a protein having serine protease inhibitory activity and a primary amino acid sequence that varies from a natural human allelic variant.

Human AAT variants can have sequences that differ from that of natural alleles by virtue of the insertion, deletion, and/or substitution of one or more amino acid residues within the sequence. Amino acid sequence variants generally will be at least about 65%, 70%, 75%, 80%, 85%, 90%, 95%, 96%, 97%, 98% or 99% identical to one of the allelic sequences described above, as determined by the percent identity reported by the BLAST 2 SEQUENCES tool using the blastp program with default parameters (Matrix: BLOSUM62; open gap penalty: 11; extension gap penalty: 1; gap x_dropoff: 50; expect: 10.0; wordsize: 3). See Tatiana et al., "Blast 2 sequences—a new tool for comparing protein and nucleotide sequences", *FEMS Microbiol Lett.* 174:247-250 (1999), incorporated herein by reference in its entirety; the tool is available for use at the National Center for Biotechnology Information (NCBI) web site. In some of the above-described embodiments, human AAT variants differ from that of natural alleles solely by conservative substitutions.

Amino acid sequence variants of AAT or of functionally active portions thereof may be naturally occurring or may be prepared synthetically, such as by introducing appropriate nucleotide changes into a previously isolated AAT DNA, or by in vitro synthesis of the desired variant polypeptide. Such variants may comprise deletions from, or insertions or substitutions of, one or more amino acid residues within the amino acid sequence of mature AAT or a functionally active portion thereof.

The sequence variants may, in various embodiments, include any combination of deletion, insertion, and substitution.

In typical embodiments, a human AAT variant of the compositions used in the methods of the present invention will have a protein sequence more similar to that of a known human AAT allele than to an AAT ortholog from any other species, as determined by using the entire human AAT variant protein sequence as query against the NCBI's protein databases using the BLASTP tool with default parameters.

AAT used in the methods of the present invention may, for example, be purified from human plasma.

PROLASTIN® (Bayer Corp.) is a sterile lyophilized preparation of native glycosylated human AAT purified from plasma pooled from normal human donors, and is approved for intravenous administration in treatment of patients with congenital deficiency of AAT and clinically demonstrable panacinar emphysema.

In addition to AAT, PROLASTIN® contains detectable levels of several proteins that copurify from plasma with AAT, including α2-plasmin inhibitor, α1-antichymotrypsin, C1 esterase inhibitor, antithrombin III, haptoglobin, albumin, α-lipoprotein, and IgA. PROLASTIN® product insert (Bayer Corp.); Coan et al., *Vox. Sang.* 48:333-342 (1985).

ARALAST™ (Alpha Therapeutic Corporation, distributed by Baxter Healthcare Corp.) is a sterile lyophilized preparation of native human glycosylated AAT purified from pooled human plasma which has also been approved for systemic therapy of hereditary emphysema.

ZEMAIRA™ (Aventis Behring LLC) is a sterile lyophilized preparation of native human glycosylated AAT purified from pooled human plasma approved for chronic augmentation and maintenance therapy in individuals with AAT deficiency and clinical evidence of emphysema.

Although AAT purified from natural sources, including any of the three above-described FDA-approved formulations of human AAT, may be used in the methods of the present invention, recombinant AAT is presently preferred, since AAT purified from plasma contains copurifying plasma proteins and presents the risk of transmitting infectious agents.

Recombinant AAT useful in the methods of the present invention will, in typical embodiments, have less than 10%, more preferably less than 5%, most preferably less than 1%, and in some embodiments, less than 0.5%, 0.4%, 0.3%, 0.2%, even less than 0.1% (as a weight percentage of protein in the composition) of any one or more of α2-plasmin inhibitor, α1-antichymotrypsin, C1 esterase inhibitor, antithrombin III, haptoglobin, albumin, α-lipoprotein, and IgA. In preferred embodiments, the AAT composition used in the methods of the present invention will completely lack one or more of α2-plasmin inhibitor, α1-antichymotrypsin, C1 esterase inhibitor, antithrombin III, haptoglobin, albumin, α-lipoprotein, or IgA In some embodiments, the AAT composition used in the therapeutic methods of the present invention contains less than 10%, 5%, most preferably less than 1%, and in some embodiments, less than 0.5%, 0.4%, 0.3%, 0.2%, even in some embodiments less than 0.1% (as a cumulative weight percentage of protein in the composition) of α2-plasmin inhibitor, α1-antichymotrypsin, C1 esterase inhibitor, antithrombin III, haptoglobin, albumin, α-lipoprotein, and IgA. In particularly preferred embodiments, the composition completely lacks each of α2-plasmin inhibitor, α1-antichymotrypsin, C1 esterase inhibitor, antithrombin III, haptoglobin, albumin, α-lipoprotein, and IgA.

In various embodiments, the cumulative weight percentage of all proteins other than AAT in the composition used in the methods of the present invention is less than 10%, 5%, most preferably less than 1%, and in some embodiments, less than 0.5%, 0.4%, 0.3%, 0.2%, even in some embodiments less than 0.1%. In particularly preferred embodiments, the composition completely lacks human plasma proteins other than AAT. In some embodiments, the composition lacks natural or recombinant surfactant proteins, either human or animal.

Thus, as a weight percentage of protein, the compositions administered in the methods of the present invention typically comprise more than 90%, 91%, 92%, 93%, 94%, even more than 95%, 96%, 97%, 98%, 99%, and in some embodiments, even more than 99.5%, AAT or active portion thereof.

Recombinant AAT used in the methods of the present invention may be prepared in any art-recognized host cell, such as bacteria, including *E. coli* (see, e.g., Kwon et al., *Biochim Biophys Acta.* 1247(2):179-84 (1995)); fungi, such as yeast, including *Saccharomyces cerevisiae* or *Pichia* species (see, e.g., Rosenberg et al., *Nature* 312:77-80 (1984); Kang et al., *Yeast* 14:371-381 (1998); and Kwon et al., *J Biotechnol.* 42(3):191-5 (1995)); plant cells (see, e.g., Terashima et al., *Appl. Microbiol. Biotechnol.* 52:516-23 (1999) and Huang et al., *Biotechnol. Prog.* 17:126-33 (2001)); insect cells, or mammalian cells (see, e.g., Garver et al., *Proc. Nat'l Acad. Sci. USA* 84:1050-4 (1987)), the disclosures of which are incorporated herein by reference in their entireties.

AAT used in the methods of the present invention—whether plasma-derived or recombinant—may be either glycosylated or unglycosylated.

By "unglycosylated" is intended that the AAT protein lacks the pattern of N-linked carbohydrates of human AAT as obtained from plasma. In typical embodiments, the AAT protein is devoid of all post-translationally added sugar moieties. In other embodiments, the AAT protein contains sugar moieties, but has no more than about 50%, 40%, 35%, 30%, 25%, 20%, 15%, 10%, 5%, 4%, 3%, 2% even no more than about 1% the sugar content, on a weight/weight basis, of human AAT as obtained from human plasma.

Unglycosylated recombinant AAT can be obtained by recombinant expression in a host that does not glycosylate the expressed protein, such as bacteria, e.g. *E. coli*, or certain yeast, or by treatment of recombinantly expressed protein expressed in hosts competent for glycosylation with one or more glycosylases. Unglycosylated AAT may also be obtained by treatment of plasma-derived AAT with glycosylases.

For example, in various embodiments of the methods of the present invention, unglycosylated recombinant human AAT may be produced in fungus, notably yeast, such as *Saccharomyces cerevisiae*, as described for example in Rosenberg et al., *Nature* 312:77-80 (1984), incorporated herein by reference in its entirety. Unglycosylated recombinant human AAT may be efficiently produced in *Saccharomyces cerevisiae* according to the methods set forth in detail in commonly owned and copending U.S. patent application Ser. No. 10/914,863, filed Aug. 9, 2004, and WO 2005/014825, the disclosures of which are incorporated herein by reference in their entireties.

The AAT used in the methods of the present invention can possess various types of alterations or derivatizations other than, or in addition to, the sequence variations described above and altered (that is, non-native patterns of) glycosylation.

In one series of embodiments, for example, the unglycosylated AAT is rAAT, a human recombinant AAT expressed in *Saccharomyces cerevisiae*. rAAT is a 395 amino acid unglycosylated protein having an amino acid sequence identical to human plasma AAT with the exception of an N-acetylmethionine residue at the amino terminus. Rosenberg et al., Nature 312:77-80 (1984), incorporated herein by reference in its entirety.

In another embodiment, the AAT is rAAT-val, an oxidation-stable unglycosylated AAT produced in *Saccharomyces cerevisiae* having an N-acetylmethionine residue at the amino terminus and sequence differing from rAAT by substitution of a valine for methionine at residue 358.

In some embodiments of the methods of the present invention, the AAT is a truncate (synonymously, fragment, portion, or domain) that retains protease inhibitory activity; such functionally active portion may be a functionally active portion of the human AAT proteins, or human AAT protein variants, described above.

In various embodiments, the functionally active portion of AAT used in the methods of the present invention is inhibitory for at least a first protease selected from the group consisting of elastase, kallikrein, cathepsin-G, trypsin, mast cell chymase, and chymotrypsin. In various embodiments, the functionally active portion of AAT used in the methods of the present invention is additionally inhibitory for at least a second protease selected from the group consisting of elastase, kallikrein, cathepsin-G, trypsin, mast cell chymase, and chymotrypsin. In typical embodiments, the AAT portion is inhibitory for the human form of the respective enzyme. In some embodiments, the functionally active portion has less protease inhibitory active than the intact protein. In other embodiments, the functionally active portion is more active in protease inhibition than the full length protein.

Functionally active portions of AAT are known in the art, Schasteen et al., *Mol. Immunol.* 28:17-26 (1991), the disclosure of which is incorporated herein by reference in its entirety, and truncates and fragments of AAT can readily be assessed for protease inhibitory activity by routine use of art-standard methods. For example, portions of AAT can readily be assessed for elastase inhibitory activity using porcine elastase-inhibition assays, such as that reported by Beatty et al., *J. Biol. Chem.* 255:3931 (1980), incorporated herein by reference in its entirety.

In certain embodiments, the functionally active portion of AAT is one of those described in U.S. Pat. Nos. 6,068,994 and 4,732,973, and in A. Hercz, "Proteolytic cleavages in alpha-one antitrypsin and microheterogeneity," *Biochem. Biophys. Res. Comm.* 128: 199-203 (1985), the disclosures of which are incorporated herein by reference in their entireties.

In other embodiments, AAT, or functionally active portion thereof, is fused to another protein, or portion thereof, and an effective amount of fusion protein administered by inhalation.

In various embodiments, the fusion protein inhibits proteases additional to those inhibited by AAT alone. In some embodiments, the protein, or portion, that is fused to AAT confers targeting activity upon the fusion protein.

In certain embodiments, the fusion is to another protease inhibitor, as is described in commonly owned and copending U.S. patent application Ser. No. 10/025,514, filed Dec. 18, 2001, published as U.S. patent application publication no. 2003/0073217, the disclosure of which is incorporated herein by reference in its entirety.

For example, AAT, or functionally active portion thereof, may be fused to secretory leukocyte protease inhibitor (SLPI), or a functionally active portion thereof. In typical such embodiments, the SLPI protein, or portion, is human SLPI.

The DNA and amino acid sequences of human SLPI were reported by Heinzel et al., *Eur. J. Biochem.* 160: 61-67 (1987), incorporated herein by reference in its entirety. Several patents describe SLPI, its nucleic acid, and/or functionally active portions of SLPI (see, e.g., U.S. Pat. Nos. 4,760,130; 5,464,822; 4,845,076; 5,633,227; 5,851,983; 5,871,956; 5,900,400; 6,017,880; and 6,291,662, the disclosures of which are incorporated herein by reference in their entireties), any of which may be used in AAT/SLPI fusion proteins in embodiments of the methods of the present invention.

In embodiments in which AAT, or functionally active portion thereof, is fused to a functionally active portion of SLPI, the functionally active portion of SLPI is inhibitory for at least a first protease selected from the group consisting of neutrophil elastase, mast cell chymase, tryptase and chymotypsin.

In certain embodiments, the protein sequence encoding AAT, or functionally active portion thereof, is joined by its C terminus to the N-terminus of SLPI, or functionally active portion thereof. In other embodiments, the protein sequence encoding AAT, or functionally active portion thereof, is joined by its N terminus to the C-terminus of SLPI, or functionally active portion thereof.

The fusion of the two proteins of the fusion protein may be by means of a simple peptide bond, or there may be one or more additional amino acids which comprise the fusion linkage between the two proteins of the fusion protein. In one embodiment, there is a methionine between the AAT and the SLPI. There may be additional sequence(s), not drawn from AAT or SLPI, in one or more locations of the fusion proteins of the invention.

In some embodiments, the methods of the present invention comprise administering an effective amount of an alpha 1-antitrypsin (AAT)/SLPI fusion protein by inhalation to the lungs of an individual having or at risk of developing COPD. The fusion protein comprises amino acids from about 1 to about 394 of AAT, and amino acids from about 1 to about 107 of SLPI. In one such embodiment, the carboxy terminus of amino acids from about 1 to about 394 of AAT is joined to the amino terminus of amino acids from about 1 to about 107 of SLPI (i.e., the fusion protein comprises, from its amino to its carboxy termini, amino acids from about 1 to about 394 of AAT fused to amino acids from about 1 to about 107 of SLPI). In another embodiment, the carboxy terminus of amino acids from about 1 to about 107 of SLPI is joined to the amino terminus of amino acids from about 1 to about 394 of AAT (i.e., the fusion protein comprises, from its amino to its carboxy termini, amino acids from about 1 to about 107 of SLPI fused to amino acids from about 1 to about 394 of AAT).

In various other embodiments, AAT, or a functionally active portion thereof, is fused to a metalloprotease inhibitor, or a functionally active portion thereof, and an effective amount of the fusion protein administered by inhalation.

In some embodiments, for example, AAT or a functionally active portion thereof is fused to a tissue inhibitor of matrix metalloproteases (synonymously, "tissue inhibitor of matrix metalloproteinases") (TIMP), or functionally active portion thereof.

In various embodiments, the TIMP is selected from TIMP-1, TIMP-2, TIMP-3, and TIMP-4. The amino acid and nucleotide sequences of all four human TIMPs have been characterized: TIMP-1 (Docherty et al., *Nature* 318: 66-69, 1985); TIMP-2 (Boone et al., *Proc. Natl. Acad. Sci.* 87:2800-2804); TIMP-3 (Wilde et al., *DNA Cell Biol.* 13: 711-718); and TIMP-4 (Hawkins et al., U.S. Pat. No. 5,643,752). The disclosures of these references are incorporated herein by reference in their entireties.

In embodiments in which AAT, or functionally active portion thereof, is fused to a functionally active portion of a TIMP, the functionally active portion of TIMP is inhibitory for at least a first protease selected from the group consisting of activated interstitial collagenase, the 92 kDa Type IV collagenase, stromelysin, gelatinases A and B, 72 kDA Type IV collagenase, collagenase 1, other gelatinases and other collagenases. In other embodiments, the functionally active portion of TIMP is inhibitory for at least a second protease selected from the same group.

In one series of embodiments, for example, AAT, or functionally active portion thereof, is fused to TIMP-1, or a functionally active portion thereof. The functionally active portion of TIMP-1 may possess protease inhibitory activity, targeting activity, or both. In some embodiments, the targeting activity is macrophage targeting activity.

In various embodiments, an N-terminal portion of TIMP-1 is use. In some embodiments, the TIMP-1 fragment is used with an initial methionine, and thus contains 127 amino acids (the initial methionine plus the N-terminal 1-126 amino acids of TIMP-1); this fragment is referred to herein as N-TIMP 1-127 (see SEQ ID NO: 22). In various embodiments, the N-terminal fragment of TIMP-1 is the first 127 N-terminal amino acids of the native form. Amino acid 127 of this latter fragment is a free cysteine, and is thus available to participate in disulfide bond formation, which is one manner of constructing the fusion proteins of the invention. In various embodiments, this latter fragment is used with an initial methionine, and thus contains 128 amino acids (the initial methionine plus the N-terminal 1-127 amino acids of TIMP-1); this fragment is referred to herein as N-TIMP 1-128 (see SEQ ID NO: 24).

In the AAT-TIMP fusion proteins of the present invention, AAT may be linked C-terminally to the N-terminus of TIMP, or TIMP may be fused C-terminally to the N-terminus of AAT. The fusion of the two moieties—that contributed by AAT and that contributed by a TIMP—may be by means of a simple peptide bond, or there may be one or more additional amino acids which comprise the fusion linkage between the two proteins of the fusion protein.

In some embodiments, the methods of the present invention comprise administering an AAT-TIMP1 fusion protein comprising amino acids from about 1 to about 394 of alpha 1-antitrypsin; and amino acids from about 1 to about 184 of tissue inhibitor of metalloproteases-1. In one such embodiment, the carboxy terminus of amino acids from about 1 to about 394 of AAT is joined to the amino terminus of amino acids from about 1 to about 184 of tissue inhibitor of metalloprotease-1 (i.e., the fusion protein comprises, from its amino to its carboxy termini, amino acids from about 1 to about 394 of AAT fused to amino acids from about 1 to about 184 of tissue inhibitor of metalloprotease-1). In another embodiment, the carboxy terminus of amino acids from about 1 to about 184 of tissue inhibitor of metalloproteases-1 is joined to the amino terminus of amino acids from about 1 to about 394 of AAT (i.e., the fusion protein comprises, from its amino to its carboxy termini, amino acids from about 1 to about 184 of tissue inhibitor of metalloproteases-1 fused to amino acids from about 1 to about 394 of AAT).

In yet other embodiments, the methods of the present invention comprise administering AAT, or functionally active portion thereof, is fused to a functionally active portion of TIMP-2. The functionally active portion of TIMP-2 may be one of those disclosed in Willenbrock et al., *Biochemistry* 32: 4330-4337, (1993).

In other embodiments, AAT, or functionally active portion thereof, is fused to a cysteine protease, or functionally active portion thereof.

In some embodiments, AAT or a functionally active portion thereof is linked to a cystatin, stefin, or kininogen, or functionally active portion thereof.

In certain embodiments, AAT or a functionally active portion thereof is linked to an aspartyl protease inhibitor, such as pepstatin, or a functionally active portion thereof.

In various embodiments, the sequence of the AAT fusion proteins useful in the methods of the present invention have a sequence selected from the group of sequences set forth in the accompanying Sequence Listing, incorporated herein by reference in its entirety.

In various embodiments, the native sequence of the individual proteins contributing to a fusion protein, e.g., AAT and TIMP-1, or functionally active portions thereof, need not be used in the fusion protein.

In such embodiments, amino acid sequence variants can be used for one or both fusion partners, or functionally active portions thereof, typically having at least about 65%, 70%, 75%, 80%, 85%, 90%, 95%, 96%, 97%, 98%, or 99% sequence identity to a naturally occurring protein—such as mature human AAT or TIMP-1 shown in Carrell et al., *Nature* 298:329-334, 1982 and Docherty et al., *Nature* 318: 66-69, 1985—as determined by the percent identity reported by the BLAST 2 SEQUENCES tool using the blastp program with default parameters (Matrix: BLOSUM62; open gap penalty: 11; extension gap penalty: 1; gap x_dropoff: 50; expect: 10.0; wordsize: 3). See Tatiana et al., "Blast 2 sequences—a new tool for comparing protein and nucleotide sequences", *FEMS Microbiol Lett.* 174:247-250 (1999), incorporated herein by reference in its entirety; the tool is available for use at the National Center for Biotechnology Information (NCBI) web site.

Production of the fusion proteins above-described is performed by well known art-accepted procedures, as further described with particularity in commonly owned U.S. patent application no. U.S. patent application Ser. No. 10/025,514, filed Dec. 18, 2001, published as U.S. patent application publication no. 2003/0073217, the disclosure of which is incorporated herein by reference in its entirety.

In the methods of the present invention, alpha 1-antitrypsin (AAT), or functionally active portion thereof, is administered by inhalation to the lungs of an individual having or at risk of developing COPD.

"Inhalation" refers to a method of administration of a compound that delivers an effective amount of the compound so administered to the tissues of the lower respiratory tract by inhalation of the subject compound by the individual being treated, thereby drawing the compound into the lung. As used herein, "administration" is synonymous with "delivery".

Any of the various means known in the art for administering therapeutically active agents by inhalation (pulmonary delivery) can be used in the methods of the present invention.

Such delivery methods are well-known in the art. See, e.g., M. Keller (1999) *Int. J Pharmaceutics* 186:81-90; M. Everard (2001) *J. Aerosol Med.* 14 (Suppl 1):S-59-S-64; Togger and Brenner (2001) *Am. J. Nursing* 101:26-32. Commercially available aerosolizers for liquid formulations, including jet nebulizers and ultrasonic nebulizers, are useful in the methods of the invention. For delivery in liquid form, liquid formulations can be directly aerosolized and lyophilized powder can be aerosolized after reconstitution. For delivery in dry powder form, the formulation may be prepared as a lyophilized and milled powder. In addition, formulations may be delivered using a fluorocarbon formulation or other propellant and a metered dose dispenser. For delivery devices and methods, see, e.g., U.S. Pat. Nos. 4,137,914; 4,174,712; 4,524,769; 4,667,688; 5,672,581; 5,709,202; 5,780,014;

5,672,581; 5,915,378; 5,997,848; 6,123,068; 6,123,936; 6,397,838, the disclosures of which are incorporated herein by reference in their entireties.

In certain embodiments, for example, nebulizers, which convert liquids into aerosols of a size that can be inhaled into the lower respiratory tract, are used, either in conjunction with a mask or a mouthpiece. Nebulizers suitable for use in certain embodiments of the methods of the present invention can be either pneumatic or ultrasonic, continuous or intermittent. A variety of nebulizers suitable for use in the methods of the present invention are available commercially from Aerogen, Inc. (Mountain View, Calif.)

In other embodiments, metered dose inhalers (MDI) known in the art are used. In yet other embodiments, dry powder delivery devices are also known and can be used.

In other embodiments, AAT, or a functionally active portion thereof, is delivered to the lungs using a device that approximates a cigarette in size and/or shape. For example, AAT, or a functionally active portion thereof, may be delivered using devices such as those disclosed in U.S. Pat. Nos. 6,637,430; 6,810,883; 6,595,209; 6,178,969; 6,178,969; 5,746,227; 5,687,746; 5,441,060; 5,287,850; 5,159,940; 5,113,855; 4,892,109; 4,765,348; 4,735,217; 4,393,884; and 4,083,372, the disclosures of which are incorporated herein by reference in their entireties.

In certain of these embodiments, AAT, or functionally active portion thereof, is admixed with tobacco. In certain embodiments, AAT, or functionally active portion thereof, is present in a mouth-proximal filter or reservoir of the device.

Depending upon the route of dose administration, AAT—or functionally active portion or fusion thereof (for purposes of the following, collectively "AAT")—may be administered in liquid or dry compositions.

Liquid compositions of AAT will typically be prepared for pulmonary (that is, inhalation) administration by thawing a frozen liquid composition or, more typically, by rehydrating (reconstituting) a dry composition.

For example, liquid compositions of AAT suitable for use in the methods of the present invention may be prepared by rehydrating (reconstituting) lyophilized preparations of plasma-derived, glycosylated, human AAT, such as PROLASTIN®, ARALAST™, or ZEMAIRA™.

In other embodiments, however, liquid compositions of AAT suitable for use in the methods of the present invention may be prepared by rehydrating (reconstituting) dried compositions comprising recombinant AAT, typically human AAT, including unglycosylated human AAT, such as rAAT, and human AAT truncates and fusions.

In one series of embodiments, for example, liquid compositions of AAT suitable for use in the methods of the present invention may be prepared by rehydrating a dry composition comprising unglycosylated recombinant alpha 1-antitrypsin (AAT) and at least one halide salt. The recombinant AAT, in typical embodiments, is recombinant human AAT, often rAAT.

In one series of embodiments, for example, the dry composition may comprise 0.1 to 2000 milliequivalents halide salt per 100 mg of unglycosylated AAT (such as human AAT, particularly rAAT), 50-500 milliequivalents, even 100-200 milliequivalents halide salt per 100 mg of unglycosylated AAT (such as human AAT, particularly rAAT).

In typical embodiments of the dry composition, the halide salt is present at a level of at least about 10 micromoles per 100 mg AAT, at least about 50 micromoles per 100 mg AAT, at least about 100 micromoles per 100 mg AAT, even at least about 200 micromoles per 100 mg AAT. In some embodiments, the halide salt is present at a level of about 200 micromoles per 100 mg AAT.

Typically, the halide salt is present at a level that does not exceed about 2000 millimoles per 100 mg AAT, 1500 millimoles per 100 mg AAT, no more than about 1000 millimoles per 100 mg AAT, no more than about 100 millimoles per 100 mg AAT, no more than about 10 millimoles per 100 mg AAT, even no more than about 1 millimole per 100 mg AAT.

In certain embodiments, the halide salt is present in the dry composition at a level of about 100-500 micromoles per 100 mg AAT.

The halide salt can, for example, be a chloride salt, a bromide salt, or an iodide salt. The cation can, e.g., be Na+, K+, or other monovalent or divalent cation.

In certain embodiments, the halide salt is NaCl. In a variety of such embodiments, the dry composition of the present invention comprises rAAT and NaCl.

In certain of these embodiments, the NaCl is present at a level of at least about 10 micromoles per 100 mg rAAT, 50 micromoles per 100 mg rAAT, even at least about 100 micromoles per 100 mg rAAT. In some of the embodiments, NaCl is present at a level of no more than about 1000 millimoles per 100 mg rAAT, no more than about 500 millimoles per 100 mg rAAT, even no more than about 250 millimoles per 100 mg rAAT. In various embodiments, NaCl is present at a level of about 200 micromoles per 100 mg rAAT.

The dry composition may comprise components additional to unglycosylated AAT and at least one species of halide salt.

In some embodiments, the composition further comprises at least one reducing agent. The at least one reducing agent may, for example, be selected from the group consisting of dithiothreitol, cysteine, glutathione, and N-acetyl cysteine (NAC).

In certain embodiments, the reducing agent is NAC.

NAC may be present, e.g., at a level of at least about 1 micromole per 100 mg AAT, at least about 10 micromoles per 100 mg AAT, even at least about 100 micromoles per 100 mg AAT. NAC is typically present in such embodiments at a level of no more than about 1000 micromoles per 100 mg AAT, no more than about 500 micromoles per 100 mg AAT, even no more than about 100 micromoles per 100 mg AAT.

The composition may, in addition or in the alternative, further comprise an antioxidant, such as ascorbic acid or L-Met, e.g., in an amount of up to 10 mM on reconstitution to 50 mg/ml AAT.

The composition may, in addition or in the alternative, further comprise agents useful in buffering the pH of the solution from which the composition is dried, and in buffering the pH of the liquid composition into which the composition is thereafter rehydrated.

The amount of buffer may be such that, upon exemplary rehydration of the composition in deionized water to 50 mg/ml AAT, the reconstituted solution has a pH of at least about 6.0, 6.1, 6.2, 6.3, 6.4, 6.5, 6.6, 6.7, 6.8, 6.9 even 7.0, 7.1, 7.2, 7.3, 7.4, 7.5 or higher. In some embodiments, the amount of buffer is such that, upon exemplary rehydration of the composition in deionized water to 50 mg/ml AAT, the reconstituted solution has a pH of no more than about 7.5, 7.4, 7.3, 7.2, 7.1, 7.0, even no more than about 6.9, 6.8, or even no more than about 6.7, 6.6, or 6.5.

For example, the composition may further comprise phosphate, citrate, histidine or combinations thereof, in some embodiments in an amount of 5-50 mM, preferably 10-20 mM upon exemplary reconstitution to 50 mg/ml AAT.

In some embodiments, the composition further comprises organic acids (and salts of organic acids) other than citric acid, including one or more of lactic acid, ascorbic acid, maleic acid, oxalic acid, malonic acid, malic acid, succinic acid, gluconic acid and glutamic acid.

In some embodiments, the composition may further comprise, in addition to unglycosylated AAT and at least one species of halide salt, one or more detergents or other surface active agents.

The dry compositions of the present invention may further comprise chelating agents (e.g. EDTA), preferably of a type and in an amount that does not significantly chelate either the cation or the anion of the halide salt of the composition.

Various embodiments will typically not comprise free sugars (that is, sugars that are not covalently linked to the AAT of the composition).

Thus, typical embodiments of the dry composition from which the liquid composition to be administered is rehydrated have less than 0.5%, 0.4%, 0.3%, 0.2%, even less than 0.1%, 0.05%, even less than about 0.01%, on a weight percentage basis, of any one or more of monosaccharides such as galactose, D-mannose, and sorbose; disaccharides such as lactose and trehalose; cyclodextrins such as 2-hydroxypropyl-β-cyclodextrin; and polysaccharides such as raffinose, maltodextrins, and dextrans; polyhydric polymers such as polyethylene glycol; and alditols, such as inositol, ribitol, galactitol, and ribitol. In presently preferred embodiments, the dry composition completely lacks free sugars.

In some embodiments in which the unglycosylated AAT completely lacks sugar moieties, the dry composition will have less than about 0.5%, 0.4%, 0.3%, 0.2%, even less than 0.1%, 0.05%, even less than about 0.01%, on a weight percentage basis, of any sugar or carbohydrate. In some embodiments, the composition will completely lack detectable sugar or carbohydrate.

AAT compositions of the invention may also include suitable excipients and other ingredients for pulmonary administration, as are known in the art. Preservatives are optionally included in the composition used in the invention to maintain the integrity of the composition.

Although the compositions of the present invention may comprise one or more agents additional to unglycosylated AAT and at least one species of halide salt, typical embodiments will typically contain as few such additional components as necessary to achieve the desired physical form, including residual moisture content, particle size, ease of rehydration, and stability.

In various embodiments, the compositions are sterile. This is readily accomplished by, for example, filtration through sterile filtration membranes.

As further described below, the dry compositions useful in the methods of the present invention are conveniently prepared by a variety of known techniques, including lyophilization and spray drying.

By whatever means prepared, the dry composition will, in typical embodiments, comprise less than about 5% residual moisture, as assessed, e.g., by the Karl Fischer coulometry method, conveniently performed on an anhydrous methanol extract of the dry composition.

In various embodiments, the dry composition comprises less than about 4.5%, 4%, 3.5%, 3%, 2.5%, 2.0%, 1.5%, 1% residual moisture. In certain embodiments, the dry composition comprises less than about 0.9%, 0.8%, 0.7%, 0.6%, 0.5% and even, in some embodiments, less than about 0.4% residual moisture.

In embodiments of the dry composition intended to be rehydrated before use—as, for example, by addition of a clinically acceptable sterile diluent, such as sterile water, saline, dextrose solution, D5 normal saline, or Ringer's solution—the particle size range may be greater than that in embodiments intended for dosing by dry powder inhalation, further described below.

In embodiments intended to be rehydrated into a liquid composition, for example, the particles can usefully have mass median diameter (MMD) of up to 10 µm, 20 µm, 30 µm, 40 µm, even up to 50 µm or more.

In embodiments intended to be rehydrated into a liquid composition before administration, the dry composition will be readily dissolvable.

In some embodiments, for example, at least 80% of the solids will dissolve at room temperature within 1 hour of addition of sufficient deionized water (or sterile water for injection) to achieve a nominal AAT concentration of 50 mg/ml; in other embodiments, at least 81%, 82%, 83%, 84%, 85% and even as much as 86%, 87%, 88%, 89% even as much as 90% of solids will dissolve within 1 hour of addition of a volume of deionized water sufficient to achieve a nominal concentration of 50 mg/ml AAT. In presently preferred embodiments, at least 91%, 92%, 93%, 94%, even as much as 95%, 96% or more of the solids will dissolve within 1 hour of addition of sufficient deionized water to achieve a nominal concentration of 50 mg/ml AAT.

In typical embodiments, the dry composition of the present invention demonstrates at least about 80%, 81%, 82%, 83%, 84%, even at least about 85%, 86%, 87%, 88%, and 89% retention of initial protease inhibitory activity upon rehydration following storage under conditions that are, or are equivalent to, 50° C. for 3 months. In certain embodiments, the dry composition of the present invention retains at least 90%, even at least 91%, 92%, 93%, 94%, and in the most preferred embodiments, even at least about 95% or more of the initial protease inhibitory activity upon rehydration following storage under conditions that are, or are equivalent to, 50° C. for 3 months.

Percent retention of initial activity (stability) can be assessed using assays known to those skilled in the art, such as in vitro elastase inhibition assays, for example using a calorimetric substrate. See, e.g., the porcine pancreatic elastase inhibition assay reported by Beatty et al., *J. Biol. Chem.* 255:3931 (1980), the disclosure of which is incorporated herein by reference in its entirety.

In various embodiments, the dry composition retains at least about 80%, 81%, 82%, 83%, 84%, even at least about 85%, 86%, 87%, 88%, and 89% of initial serine protease inhibitory activity, upon rehydration following storage under conditions that are, or are equivalent to, 2 years at $\leq 5°$ C. In certain embodiments, the dry composition of the present invention demonstrates at least 90%, even at least 91%, 92%, 93%, 94%, and in the most preferred embodiments, even at least about 95% or more of the initial serine protease inhibitory activity upon rehydration following storage under conditions that are, or are equivalent to, 2 years at $\leq 5°$ C.

In preferred embodiments, the dry composition retains at least about 90% of initial serine protease inhibitory activity for more than 2 years at $\leq 5°$ C., even as much as 3 years at $\leq 5°$ C.

In various embodiments, the dry compositions demonstrate low levels of AAT denaturation. Denaturation can be monitored by evaluation of aggregate formation, and the non-denatured AAT usefully reported as percent monomer using a size exclusion chromatography (SEC) HPLC method.

In typical embodiments, the AAT remains about 80%, 81%, 82%, 83%, 84%, even at least about 85%, 86%, 87%, 88%, and 89% monomeric following storage under conditions that are, or are equivalent to, 50° C. for 3 months. In some embodiments, the AAT remains at least about 90%, even at least 91%, 92%, 93%, 94%, and in the most preferred embodiments, even at least about 95% or more monomeric following storage under conditions that are, or are equivalent to, 50° C. for 3 months.

In typical embodiments, the AAT remains about 80%, 81%, 82%, 83%, 84%, even at least about 85%, 86%, 87%, 88%, and 89% monomeric following storage under conditions that are, or are equivalent to, $\leq$5° C. for 2 years. In certain embodiments, the AAT remains at least about 90%, even at least 91%, 92%, 93%, 94%, and in the most preferred embodiments, even at least about 95% or more monomeric following storage under conditions that are, or are equivalent to, $\leq$5° C. for 2 years.

The above-described dry composition may be prepared by drying a liquid composition comprising unglycosylated AAT and at least one species of halide salt sufficiently to achieve a residual moisture content of less than about 2%.

In typical embodiments, the liquid composition is dried sufficiently to achieve a residual moisture content of no more than about 2.0%, 1.9%, 1.8%, 1.7%, 1.6%, 1.5%, 1.4%, 1.3%, 1.2%, 1.1%, and even no more than about 1.0%, with various embodiments having even less residual moisture. Such embodiments may have a residual moisture content of no more than about 0.9%, 0.8%, 0.7%, 0.6%, even as low as no more than about 0.5%, or even lower.

As would be understood, the unglycosylated AAT present in the liquid composition can be any of the species that are described above as being present in the resulting dried composition, including unglycosylated human AAT, such as rAAT, functionally active portions of human AAT, and AAT fusion proteins (both glycosylated and unglycosylated) such as proteins comprising AAT, or functionally active portion of AAT, and a protease inhibitor selected from the group comprising SLPI, TIMP-1, TIMP-2, TIMP-3, TIMP-4, a cysteine protease inhibitor, and an aspartyl protease inhibitor, or functionally active portion thereof.

In typical embodiments, the unglycosylated AAT is present in the liquid composition to be dried at a concentration of at least 10 mg/ml, at least 25 mg/ml, 30 mg/ml, 35 mg/ml, 40 mg/ml, 45 mg/ml, even at least about 50 mg/ml, or even higher. In certain embodiments, the unglycosylated AAT is present in the liquid composition intended to be dried at a concentration of at least 60 mg/ml, 70 mg/ml, 80 mg/ml, 90 mg/ml even 100 mg/ml or more.

Typically, the unglycosylated AAT is present in the liquid composition intended to be dried at a concentration of less than about 200 mg/ml, more typically at a concentration of 100 mg/ml or less, even 75 mg/ml or less.

In certain embodiments, the liquid composition from which the composition is dried comprises unglycosylated AAT at a concentration of 30-70 mg/ml, more preferably 40-60 mg/ml, most preferably about 50 mg/ml.

The at least one species of halide salt can be any of the halide salts described above as present in the resulting dried compositions of the present invention, including NaCl.

In typical embodiments, the at least one halide salt is present in the liquid composition, prior to drying, at a concentration of at least about 1 mM, 5 mM, 10 mM, 15 mM, 20 mM, 25 mM, 30 mM, 35 mM, 40 mM, 45 mM, even at least about 50 mM, 60 mM, 70 mM, 80 mM, 90 mM, and even higher, including 100 mM, 110 mM, 120 mM, 130 mM, 140 mM, 150 mM, 160 mM, 170 mM, 180 mM, 190 mM, 200 mM or more. In various embodiments, the halide salt is present in the initial solution at a concentration of no more than about 300 mM, typically no more than about 250 mM, 200 mM, 150 mM, 100 mM, or even lower. In certain particularly useful embodiments, the solution from which the composition is dried comprises halide salt at a concentration of 50-150 mM, more preferably 75-125 mM, most preferably at a concentration of about 100 mM.

In some embodiments, the at least one halide salt is present in the liquid composition at a concentration of at least 110 mM, 120 mM, 130 mM, 140 mM, 150 mM, 160 mM, 170 mM, 180 mM, 190 mM, even at least about 200 mM, 250 mM, 300 mM, 350 mM, 400 mM, 450 mM, 500 mM or more.

Typically, the at least one halide salt is present in the liquid composition at a concentration of no more than about 500 mM, 450 mM, 400 mM, 350 mM, even no more than about 300 mM. In some embodiments, the at least one halide salt is present in the liquid composition at a concentration of no more than about 250 mM, 200 mM, 150 mM, even in some instances no more than about 100 mM.

In some embodiments, the pH of the liquid composition is buffered, and the dry compositions are prepared by drying a solution comprising unglycosylated AAT and at least one halide salt buffered to a pH of at least 6.5, 6.6, 6.7, 6.8, 6.9, even at least 7.0, 7.1, 7.2, 7.3, 7.4 or 7.5. In various embodiments, the solution to be dried is buffered to a pH of no more than about 7.5, 7.4, 7.3, 7.2, 7.1, even no more than about 7.0, 6.9, 6.8, 6.7, 6.6, or 6.5. In presently preferred embodiments, the composition of the present invention is dried from a solution buffered to a pH of 6.6-7.0, more preferably 6.7-6.9, most preferably 6.8±0.1.

The buffer can, in some embodiments, be a phosphate buffer, a citrate buffer, a histidine buffer, or combinations thereof.

As would be understood from the description of the dry compositions set forth above, the liquid composition from which the dry composition is prepared may further comprise a reducing agent, such as a reducing agent selected from the group consisting of dithiothreitol, cysteine, glutathione, and N-acetyl cysteine (NAC), and/or an antioxidant.

As would also be understood from the description of the dry compositions of the invention hereinabove, in typical embodiments the liquid composition from which the dry composition is prepared lacks detectable sugars, including free sugars and/or sugars covalently pending from the AAT protein, and is free from human serum proteins other than AAT, such as $\alpha$2-plasmin inhibitor, $\alpha$1-antichymotrypsin, C1 esterase inhibitor, antithrombin III, haptoglobin, albumin, $\alpha$-lipoprotein, and IgA.

In embodiments in which recombinantly expressed unglycosylated AAT, such as rAAT, is used, the liquid composition to be dried does not require viral inactivation, either by heating, e.g., at 60° C. or 65° C., or by treatment with solvent detergent mixtures and/or nanofiltration. Neither does the solution obtained therefrom after drying and subsequent rehydration.

Tables 1A, 1B, and 1C present exemplary AAT formulations that can usefully be dried, as by lyophilization or spray drying, and then either (i) reconstituted for use in liquid dosing (e.g., administration by nebulization or aerosolizing metered dose inhaler) or (ii) used directly for doses to be administered by dry powder inhalation in the methods of the present invention.

TABLE 1A

Formulation of Lyophilization Candidates

| Form. | mg/ml rAAT | PH | MM NaPi | mM NaCl | % Trehalose | mM L-met | mM NAC | mM Citrate | % Tween 80 |
|---|---|---|---|---|---|---|---|---|---|
| 1 | 50 | 7.4 | 10 | 0 | 2.5 | 5 | 0 | 0 | 0.1 |
| 2 | 50 | 6.8 | 10 | 100 | 0 | 0 | 0 | 0 | 0 |
| 3 | 50 | 6.8 | 20 | 100 | 0 | 0 | 5 | 1 | 0 |
| 4 | 50 | 6.8 | 10 | 100 | 0 | 3 | 0 | 0 | 0 |

TABLE 1B

Formulations

| Sample ID | [rAAT] mg/ml | pH | NaPi mM | His MM | NaCl mM | Citrate MM | NAC mM | L-met mM |
|---|---|---|---|---|---|---|---|---|
| 917-1 | 50 | 7 | 20 | 0 | 175 | 5 | 2.5 | 3 |
| 917-3 | 50 | 7 | 20 | 0 | 100 | 5 | 2.5 | 3 |
| 917-4 | 50 | 7 | 20 | 0 | 50 | 5 | 2.5 | 3 |
| 917-11 | 50 | 7.4 | 20 | 0 | 0 | 0 | 0 | 0 |

TABLE 1C

Formulations

| Formulation | pH | [rAAT] mg/mL | NaPi Mm | NaCl Mm | NAC mm | Citrate Mm | L-Met Mm |
|---|---|---|---|---|---|---|---|
| ARV-8 | 6.8 | 10 | 10 | 100 | 0 | 0 | 3 |
| ARV-9 | 6.8 | 10 | 10 | 100 | 2.5 | 5 | 3 |
| ARV-13 | 6.8 | 10 | 10 | 100 | 5 | 1 | |

In other embodiments, the dry composition further comprises, in addition to AAT, a sugar.

In such embodiments, the dry AAT composition typically comprises a simple carbohydrate (e.g., a mono-, di- or trisaccharide). The carbohydrate functions, among other things, as an amorphous cryoprotectant and lyoprotectant, thus facilitating room temperature storage. The carbohydrate is selected to be compatible with lung tissue and, for formulations that are to be nebulized after rehydration, is selected to be compatible with nebulization. Various carbohydrates can be used in certain alternative formulations. Other suitable carbohydrates include, but are not limited to, lactose, sucrose, raffinose and maltodextrin. Still other formulations include monosaccharides such as sorbose or galactose, or alditols like xylitol or mannitol.

In these embodiments, the concentration of the carbohydrate in liquid formulation prior to drying generally ranges from about 1 mg/ml to about 50 mg/ml, and in other instances about 10 mg/ml to about 50 mg/ml. Various formulations contain at least 1, 5, 10, 15, 20, 25, 30, 35, 40 or 45 mg/ml carbohydrate, but generally less than about 50 mg/ml.

Whether lacking sugars or containing sugars, the dry composition may be prepared by drying a liquid composition using methods well known in the art, such as: lyophilization; spray drying; lyophilization followed by milling to micronize the lyophilisate; atomization onto a cold surface, followed by sublimation and collection of the micronized powder; evaporative drying of a non-frozen solution in a vacuum oven or centrifugal evaporator maintained at temperatures where the solution does not freeze, followed by milling; spray coating; spray freeze-drying; fluidized bed drying; super critical fluid drying; agglomeration; extrusion, and combinations thereof. See, e.g., Maa et al., "Biopharmaceutical powders: particle formation and formulation considerations," Curr. Pharm. Biotechnol. 1:283-302 (2000), the disclosure of which is incorporated herein by reference in its entirety.

Lyophilization may usefully be used to prepare AAT for direct use, or subsequent rehydration and liquid use, in the methods of the present invention. Lyophilization finds particular use in embodiments in which the dry composition is intended for rehydration before use.

Protein lyophilization methods are known in the art. See, e.g., Carpenter et al., "Rational design of stable lyophilized protein formulations: theory and practice," Pharm. Biotechnol. 13:109-133 (2002); Carpenter et al., "Rational design of stable lyophilized protein formulations: some practical advice," Pharm Res. 14(8):969-75 (1997); Rey et al. (eds.), Freeze-Drying/Lyophilization of Pharmaceutical and Biological Products (Drugs and the Pharmaceutical Sciences: a Series of Textbooks and Monographs), Marcel Dekker (2nd rev. & ex. edition, 2004) (ISBN: 0824748689), the disclosures of which are incorporated herein by reference in their entireties.

Lyophilization apparatuses are commercially available. For example, lyophilization can be performed using a Genesis Pilot-scale Virtis 12XL lyophilizer equipped with three stoppering shelves and an external condenser. Parameters such as ramp rate, shelf-temperature, time, and vacuum can be programmed into the cycle run and the product temperatures recorded using four available thermocouples by the Wizard control system software provided by the Virtis Company.

The lyophilization cycle can usefully be one typically used for amorphous formulations, as shown below in Table 2.

TABLE 2

Exemplary Lyophilization Cycle

| Step | Temperature | Time (min) | Ramp/Hold |
|---|---|---|---|
| Freezing | +5° C. | 60 | Hold |
| | −45° C. | 100 | Ramp |
| | −45° C. | 240 | Hold |
| Drying at 100 mT chamber pressure | −45° C. | 60 | Hold |
| | −15° C. | 240 | Ramp |
| | −15° C. | 1150 | Hold |
| | +40° C. | 240 | Ramp |
| | +40° C. | 600 | Hold |

Such a lyophilization cycle is a conservative cycle with primary drying performed at a shelf temperature of −15° C. that maintains the product temperature around −30° C., well below the collapse temperature of typical formulations of the present invention (eutectic melting temperature of NaCl). In this cycle, moisture content is minimized by raising the secondary drying temperature to 40° C. for a period of 10 hours.

Production scale lyophilization apparatuses are also available commercially.

Spray drying may also usefully be used in the preparatory methods of the present invention, and has particular use for embodiments in which at least one dose of AAT is to be administered by dry powder inhalation.

Spray-drying typically comprises a three-step process resulting in dry particle formation. The process begins by atomizing a liquid feed into a spray of fine droplets using compressed air, followed by heating media in order to dry the droplets by evaporating the moisture content of the droplets. The final particles, in the form of dry powder, are collected as product; the gas and the excess fine dust are exhausted. These steps are carried out using three components: the atomizer in shape of a nozzle; the drying chamber; and the collecting system known as cyclone and pot.

Spray drying apparatuses are available commercially. For example, spray drying in the methods of the present invention can usefully be performed using a Büchi® spray drier B-191 or B-290 (Brinkmann Instruments, Inc.).

Spray drying may optionally be followed by further drying, and optionally by agglomeration. Spray drying may usefully be performed, e.g., as described in U.S. Pat. Nos. 5,780,014; 6,258,341; 6,309,671, and 6,589,560, and European patent no. EP 0941067 B1, the disclosures of which are incorporated herein by reference in their entireties.

Spray coating may also be performed to prepare dry AAT compositions for use in the methods of the present invention, and may be performed using standard techniques. See, e.g., Maa et al., "Spray-coating for biopharmaceutical powder formulations: beyond the conventional scale and its application," Pharm Res. 21(3):515-23 (2004), incorporated herein by reference in its entirety.

Dry AAT compositions may be reconstituted into a liquid form by addition of sterile diluent—such as sterile water, saline, D5, D5 normal saline, or Ringer's solution—for administration of doses by aerosolization, as by nebulization or metered dose inhaler.

Dry AAT compositions may, in the alternative, be used directly for administration of doses by dry powder inhalation.

In other embodiments, AAT is formulated for dry powder inhalation according to any one of U.S. Pat. Nos. 5,780,014; 5,993,783; 6,258,341; 6,309,671, and 6,589,560 and corresponding European patent no. EP0941067B1, the disclosures of which are incorporated herein by reference in their entireties.

Whether delivered as a liquid aerosol or a dry powder, the AAT particle size upon inhalation is usefully less than about 5 μm MMAD (mass median aerodynamic diameter), although particles larger than 5 μm MMAD can be used, including particles as large as about 6 μm, 7 μm, 8 μm, even 9 μm, 10 μm MMAD or more. In various embodiments, the particles are usefully less than about 4 μm MMAD, 3 μm MMAD, and can even be less than about 2 μm MMAD, 1.9 μm MMAD, 1.8 μm MMAD, 1.7 μm MMAD, 1.6 μm MMAD, even 1.5 μm MMAD or smaller. In some embodiments, the particles are usefully less than about 1.4 μm MMAD, 1.3 μm MMAD, 1.2 μm MMAD, 1.1 μm MMAD, even less than about 1.0 μm MMAD, or smaller. For dry particles, MMAD determinations are usefully made using a cascade impactor.

In various such embodiments, the particles can be at least about 0.5, 0.6, 0.7, 0.8, 0.9, or even at least about 1 μm MMAD, 2 μm MMAD, even at least 3 μm MMAD or more. Typically, the particles will range from 1 μm to 5 μm MMAD for doses to be administered by dry powder inhalation.

In various embodiments, the particles can usefully be less than about 5 μm MMD (mass median diameter). In other such embodiments, the particles are usefully less than about 4 μm MMD, 3 μm MMD, and can even be less than about 2 μm MMD, 1 μm MMD, 0.9 μm MMD, 0.8 μm MMD, 0.7 μm MMD, 0.6 μm MMD, even 0.5 μm MMD or smaller. In various such embodiments, the particles can be at least about 0.5 μm MMD, 0.6 μm MMD, 0.7 μm MMD, 0.8 μm MMD, 0.9 μm MMD, 1 μm MMD, 2 μm MMD, even at least 3 μm MMD or more. Typically, the particles will range from 1 μm to 5 μm MMD. For dry particle embodiments, MMD determinations can usefully be made using centrifugal sedimentation techniques (e.g., using the Horiba Particle Size Analyzer—Model CAPA-700).

Dry powder particles may be further agglomerated to facilitate delivery to an inhaler, as described, e.g., in U.S. Pat. Nos. 5,780,014 and 5,993,783, the disclosures of which are incorporated herein by reference in their entireties. In such embodiments, the agglomerates are dispersible into component particles having particle diameters (MMAD) of about 1 μm-about 5 μm.

The methods of the present invention comprise administering an effective amount of alpha 1-antitrypsin (AAT), or functionally active portion or fusion thereof, to an individual having or at risk of developing COPD. In various embodiments, the individual is a vertebrate. In certain of these embodiments, the individual is a mammal. Mammals include, but are not limited to, farm animals, sport animals, pets, primates, horses, dogs, cats, mice and rats. In typical embodiments, however, the individual is a human.

In various embodiments of the present invention, AAT, or functionally active portion or fusion thereof, is administered to an individual whose lungs are periodically exposed to at least one airborne agent capable of oxidizing AAT. For example, in certain embodiments the individual is periodically exposed to tobacco smoke, either second-hand or directly from smoking a tobacco product. In certain embodiments, the individual smokes cigarettes.

The appropriate dosage regimen, i.e., dose, timing and repetition, of AAT will depend, in various embodiments, on any one or more of the identity of the AAT protein administered (e.g., whether glycosylated or unglycosylated, entirety or functionally active portion thereof, or fusion thereof), whether the AAT is administered in combination with other active ingredients, as further described below, the formulation used (especially whether the formulation is a liquid or dry powder), whether the AAT is administered for preventive (synonymously, prophylactic) or for therapeutic purposes, the type and severity of the COPD (with or without underlying emphysema) to be treated or prevented, previous therapy, the patient's clinical history and response to the agent, genetic factors such as known AAT deficiency, and the discretion of the attending physician, if the individual is under the care of a physician.

A single dose or repeated doses may be given of AAT.

For repeated administrations over several days or longer, depending on the condition, the treatment is sustained until a desired suppression of disease symptoms occurs or until sufficient levels of AAT and other active ingredients, if used, are achieved to produce a therapeutic effect and/or to reduce the risk of COPD or emphysema under the environmental conditions to which the treated individual is exposed. In some embodiments, the dosage regimen is designed to reduce the risk of COPD in a smoker.

A "smoker," as used herein, is an individual who is exposed to tobacco smoke, whether occasionally or frequently, and whether as the result of direct use of tobacco products, or as the result of inhalation of secondhand tobacco smoke. A "former smoker" is an individual who has in the past been exposed to tobacco smoke, whether occasionally or frequently, and whether as the result of direct use of tobacco products, or as the result of inhalation of secondhand tobacco smoke.

In some embodiments, the dosage regimen is designed to reduce the risk of emphysema in a smoker or former smoker. In the case of treatment of established COPD (with or without underlying emphysema), the progress of therapy is easily monitored by conventional techniques and assays.

In the case of prevention of COPD or emphysema, e.g., in smokers, the treatment may continue indefinitely, e.g., as long as exposure to tobacco smoke lasts.

The dosing regimen can vary over time, and may be adjusted according to disease progression, remission, or exacerbation, according to exposure to environmental factors that cause or aggravate COPD or emphysema, or a combination of these.

In various embodiments of the invention, the daily dose of AAT (or functionally active portion or fusion thereof) is at least about 1 mg, 2 mg, 3 mg, 4 mg, 5 mg, 6 mg, 7 mg, 8 mg, 9 mg, 10 mg, 15 mg, 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, even at least about 410 mg, 420 mg, 430 mg, 440 mg, 450 mg, 460 mg, 470 mg, 480 mg, 490 mg, 500 mg. In some embodiments, the daily dose of AAT is at least about 510 mg, 520 mg, 530 mg, 540 mg, 550 mg, 560 mg, 570 mg, 580 mg, 590 mg, 600 mg, 610 mg, 620 mg, 630 mg, 640 mg, 650 mg, or even more.

In some embodiments, the daily dose of AAT (or functionally active portion or fusion thereof) is no more than about 700 mg, 690 mg, 680 mg, 670 mg, 660 mg, 650 mg, 640 mg, 630 mg, 620 mg, 610 mg, 600 mg, in some embodiments even no more than about 590 mg, 580 mg, 570 mg, 560 mg, 550 mg, 540 mg, 530 mg, 520 mg, 510 mg, 500 mg, 490 mg, 480 mg, 470 mg, 460 mg, 450 mg, 440 mg, 430 mg, 420 mg, 410 mg, 400 mg, even in some embodiments less.

In various embodiments, the daily dose of AAT (of functionally active portion or fusion thereof) is from about 1 mg to about 650 mg, or from about 5 mg to about 200 mg, or from about 5 mg to about 100 mg, or from about 10 mg to about 80 mg, or from about 25 mg to about 70 mg, or about 65 mg, in liquid solution or as a dry powder. In one embodiment the daily dose of AAT is about 65 mg.

In embodiments in which AAT is present as part of a fusion protein with TIMP or SLPI, the dosages may be adjusted to take into account the additional presence of the TIMP or SLPI moiety.

As will be appreciated by the skilled artisan, the size of a single dose of AAT to be delivered by pulmonary administration (synonymously, by inhalation) depends on the form of AAT used (i.e., liquid or dry powder), the likely volume to be inhaled, and, in the case of a liquid, the solubility of the AAT.

In various embodiments of the methods of the present invention, at least one individual dose is at least about 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.1. mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 15 mg, 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, even at least about 410 mg, 420 mg, 430 mg, 440 mg, 450 mg, 460 mg, 470 mg, 480 mg, 490 mg, 500 mg. In some embodiments, the daily dose of AAT is at least about 510 mg, 520 mg, 530 mg, 540 mg, 550 mg, 560 mg, 570 mg, 580 mg, 590 mg, 600 mg, 610 mg, 620 mg, 630 mg, 640 mg, 650 mg, or even more.

In various embodiments of the methods of the present invention, at least one individual dose is no more than about 700 mg, 690 mg, 680 mg, 670 mg, 660 mg, 650 mg, 640 mg, 630 mg, 620 mg, 610 mg, 600 mg, in some embodiments even no more than about 590 mg, 580 mg, 570 mg, 560 mg, 550 mg, 540 mg, 530 mg, 520 mg, 510 mg, 500 mg, 490 mg, 480 mg, 470 mg, 460 mg, 450 mg, 440 mg, 430 mg, 420 mg, 410 mg, 400 mg, and even in some embodiments less. In some embodiments, at least one individual dose is less than about 300 mg, 200 mg, 100 mg, 50 mg, 20 mg, 12 mg, 8 mg, 6 mg, 4 mg, 2 mg, in some embodiments even less than about 1.0 mg, 0.5 mg, and even, in some embodiments, less than about 0.1 mg.

In certain embodiments, AAT (or functionally active portion of fusion thereof) is self-administered. An individual, such as a smoker, may, for example, administer the AAT formulation in the morning, or periodically throughout the day, or before each exposure to tobacco smoke. It will be readily apparent to one of skill in the art that the dose size may be adjusted to account for the frequency and timing of administration of the AAT, and that the daily dosage may, to some degree, be determined by the individual or a clinician based on estimated exposure to tobacco smoke and the type of exposure (e.g., passive or active), on the delivery system used (e.g., dosage required in a dry powder formulation can be different, e.g., lower, than those in a liquid nebulizer; dosage in a metered dose inhaler may also require adjustment), and on the presence or absence of other risk factors (e.g., hereditary risk factors for COPD or emphysema, or other environmental risk factors such as occupational risk factors and/or exposure to air pollution).

In various embodiments, it may be desirable to place an upper limit on single doses and/or daily dosage. Administration devices that limit or modulate self administration of pulmonarily-administered pharmaceuticals and other substances in order to prevent possible overdose by the individual are well-known in the art.

Dose frequency may be from once daily, twice daily, or three times daily, to twice daily, four times daily, six times daily, eight times daily, or more than eight times daily. In some embodiments, the dose frequency is from once daily to six times daily, or once daily to four times daily, or once daily, or twice daily. Frequency of administration may be determined and adjusted over the course of treatment or prevention, and is generally, but not necessarily, based on treatment and/or suppression and/or amelioration and/or delay of symptoms and clinical findings. In the case of prevention of COPD (with or without underlying emphysema), in an individual exposed to environmental conditions that increase the likelihood of COPD or emphysema, frequency of administration may be modulated based on the frequency and/or severity of exposure.

In one embodiment of the invention, smokers self-administer the formulations of the invention at a frequency that depends on the frequency of tobacco smoking or exposure to secondhand smoke. The size and frequency of dosage may be determined at the discretion of a clinician, depending on factors previously discussed.

In some embodiments, the methods of the present invention further comprise administering an effective amount of at least a second protease inhibitor, or functionally active portion thereof, by inhalation to the lungs.

In some embodiments, the second protease inhibitor is an inhibitor of a metalloprotease, such as a matrix metalloprotease. In some embodiments, the inhibitor is selected from the group consisting of SLPI, TIMP-1, TIMP-2, TIMP-3, and TIMP-4. In another embodiment, the inhibitor is ilomastat.

In some embodiments, the second protease inhibitor or functionally active portion thereof is administered in common formulation with AAT or functionally active portion thereof.

In other embodiments, the second protease inhibitor or functionally active portion thereof is administered in a composition separate from that containing AAT or functionally active portion thereof. In some of these latter embodiments, the dosage schedule is the same as the dosage schedule for administration of AAT or functionally active portion thereof. In others of these embodiments, the second protease inhibitor is administered on a different dosage schedule from that used for AAT or functionally active portion thereof.

In some embodiments, the methods of the present invention further comprise administering at least a first active agent that ameliorates one or more symptoms of COPD.

The at least first active agent may, in some embodiments, be a bronchodilator.

In some embodiments, the bronchodilator is administered in common formulation with AAT, or functionally active portion or fusion thereof. In other embodiments, the bronchodilator is administered in a composition separate from that containing AAT or functionally active portion or fusion thereof. In some of these latter embodiments, the bronchodilator is administered by inhalation on a dosage schedule that is the same as the dosage schedule for administration of AAT or functionally active portion or fusion thereof. In others of these embodiments, the bronchodilator is administered on a different dosage schedule from that used for AAT or functionally active portion or fusion thereof. In various embodiments, the bronchodilators are administered orally.

In various embodiments, the bronchodilator is selected from bronchodilators currently in clinical use for treatment of COPD. The bronchodilator may, for example, be selected from those listed in Table 3.

TABLE 3

| Bronchodilators for Treatment of COPD | | | | | |
|---|---|---|---|---|---|
| Drug | Inhaler ($\mu$g) | Solution for Nebulizer (mg/ml) | Oral | Vials for Injection (mg) | Duration of Action (hours) |
| Short-acting $\beta_2$-agonists | | | | | |
| Fenoterol | 100-200 (MDI) | 1 | 0.05% (Syrup) | | 4-6 |
| Salbutamol (albuterol) | 100, 200 (MDI & DPI) | 5 | 5 mg (Pill) Syrup 0.024% | 0.1, 0.5 | 4-6 |
| Terbutaline | 400, 500 (DPI) | — | 2.5, 5 (Pill) | 0.2, 0.25 | 4-6 |
| Long-acting $\beta_2$-agonists | | | | | |
| Formoterol | 4.5-12 (MDI & DPI) | | | | 12+ |
| Salmeterol | 25-50 (MDI & DPI) | | | | 12+ |
| Short-acting anticholinergics | | | | | |
| Ipratropium bromide | 20, 40 (MDI) | 0.25-0.5 | | | 6-8 |
| Oxitropium bromide | 100 (MDI) | 1.5 | | | 7-9 |
| Long-acting Anticholinergics | | | | | |
| Tiotropium | 18 (DPI) | | | | 24+ |
| Combination short-acting $\beta_2$-agonists plus anticholinergic in one inhaler | | | | | |
| Fenoterol/ Ipratropium | 200/80 (MDI) | 1.25/0.5 | | | 6-8 |
| Salbutamol/ Ipratropium | 75/15 (MDI) | 0.75/4.5 | | | 6-8 |
| Methylxanthines | | | | | |
| Aminophylline | | | 200-600 mg (Pill) | 240 mg | Variable, up to 24 |
| Theophylline (SR) | | | 100-600 mg (Pill) | | Variable, up to 24 |

MDI = metered dose inhaler;
DPI = dry powder inhaler

As used herein, the terms "ipratropium" and "tiotropium" include, but are not limited to, any form of ipratropium or tiotropium which is capable of producing a desired bronchodilation effect in patients suffering from COPD or emphysema, including, but not limited to, all tautomeric forms, enantiomeric forms, stereoisomers, anhydrides, acid addition salts, base salts, solvates, analogues and derivatives of ipratropium or tiotropium. In the present invention, acceptable salts of ipratropium or tiotropium may include, but are not limited to, halide salts such as bromide, chloride and iodide. In one embodiment of the present invention, the preferred salt of ipratropium or tiotropium is bromide.

The at least first active agent may, in some embodiments, be a corticosteroid.

In some embodiments, the corticosteroid is administered in common formulation with AAT, or functionally active portion or fusion thereof. In other embodiments, the corticosteroid is administered in a composition separate from that containing AAT or functionally active portion or fusion thereof. In some of these latter embodiments, the corticosteroid is administered by inhalation on a dosage schedule that is the same as the dosage schedule for administration of AAT or functionally active portion or fusion thereof. In others of these embodiments, the corticosteroid is administered on a different dosage schedule from that used for AAT or functionally active portion or fusion thereof. In various embodiments, the corticosteroids are administered orally.

In various embodiments, the corticosteroid is selected from corticosteroids currently in clinical use for treatment of COPD. The corticosteroid may, for example, be selected from those listed in Table 4.

TABLE 4

Corticosteroids for Treatment of COPD

| Inhaled glucocorticosteroids | | |
|---|---|---|
| Beclomethasone | 100, 250, 400 (MDI & DPI) | 0.2-0.4 |
| Budesonide | 100, 200, 400 (DPI) | 0.20, 0.25, 0.5 |
| Fluticasone | 50-500 (MDI & DPI) | |
| Triamcinolone | 100 (MDI) | 40 | 40 |
| Combination long-acting $\beta_2$-agonists plus glucocorticosteroids in one inhaler | | |
| Formoterol/ Budesonide | 4.5/80, 160 (DPI) (9/320) (DPI) | |
| Salmeterol/ Fluticasone | 50/100, 250, 500 (DPI) 25/50, 125, 250 (MDI) | |
| Systemic glucocorticosteroids | | |
| Prednisone | 10-2000 mg | 5-60 mg (Pill) |
| Methyl-prednisolone | | 4, 8, 16 mg (Pill) |

MDI = metered dose inhaler;
DPI = dry powder inhaler

Corticosteroids useful in various embodiments of the methods of the present invention include, for example, beclomethasone dipropionate, triamcinolone acetonide, fluticasone propionate. In various embodiments, combinations of corticosteroids are used.

In other embodiments, the methods further comprise administration of one or more of mucolytics/expectorants for mucus regulation, and antibiotics for the management of infection, if present.

In other embodiments, the methods further comprise administering one or more inhibitors of various steps of the arachidonic acid pathway, or interactions of metabolites in that pathway with their cognate receptors.

For example, in various embodiments, the methods of the present invention further comprise agents that affect the synthesis or activity of one or more leukotrienes.

In some embodiments, for example, the agent is an inhibitor of leukotriene synthesis. In various of these embodiments, the agent is an inhibitor of 5-lipoxygenase. In a number of these latter embodiments, the agent is zileuton (ZYFLO). In certain embodiments, the agent is administered orally.

In other embodiments, the agent is a leukotriene receptor antagonist. In some of these embodiments, the agent is montelukast (SINGULAIR), a selective leukotriene receptor antagonist that inhibits the cysteinyl leukotriene CysLT1 receptor, or zafirlukast (ACCOLATE), a synthetic, selective peptide leukotriene receptor antagonist. In various embodiments, the agent is administered orally.

In some embodiments, the agent is an inhibitor of phosphodiester 4 (PDE4). In certain of these embodiments, the agent is roflumilast (DAXAS). In other embodiments, the inhibitor is cilomilast. In yet other embodiments, the inhibitor is BAY 19-8004. In some exemplary embodiments, the PDE4 inhibitor is administered orally.

In other embodiments, the methods of the present invention further comprise administering cromolyn or nedocromil. In certain embodiments, the agent is administered by inhalation.

The protease inhibitor compositions for use in the methods of the present invention may be provided in any suitable container known in the art or apparent to the ordinarily skilled artisan. Compositions may be prepared in unit dosage form, e.g., at the dosages given above, or in multiples of those dosages, for use in inhalation delivery devices, such as nebulizers, metered dose inhalers, and dry powder inhalers, as is common in the art. See, e.g., U.S. Pat. Nos. 4,137,914; 4,174,712; 4,524,769; 4,667,688, 5,780,014, 5,672,581; 5,915,378; and 5,997,848, the disclosures of which are incorporated herein by reference in their entireties.

In another aspect, the invention provides kits for treating chronic obstructive pulmonary disease (COPD).

The kits comprise at least one dose of at least one composition for use in the methods of the present invention. In certain embodiments, for example, the kit comprises at least one dose of AAT, a functionally active portion of AAT, or a fusion protein comprising AAT or a functionally active portion thereof. In certain of these embodiments, the fusion comprises SLPI, or a functionally active portion thereof; in other embodiments, the fusion comprises TIMP-1, or a functionally active portion thereof.

In various embodiments, the kit further comprises at least one device for delivering at least one dose by inhalation.

For example, the kit may comprise a nebulizer suitable for aerosolization of the composition. In other embodiments, the kit comprises a metered dose inhaler. In yet other embodiments, the kit comprises a dry powder inhaler. The one or more doses may be prior-loaded into the delivery device or may be separately packaged.

In embodiments comprising a nebulizer, the one or more doses may be dry, and the kit further comprise sterile diluent to be used to rehydrate the dried composition. The sterile diluent typically will be separately packaged in a container that maintains sterility, such as an ampule or vial. In various embodiments the diluent is selected from the group comprising sterile water, saline, dextrose solution, D5 normal saline, and Ringer's solution.

In embodiments comprising a metered dose inhaler, the metered dose inhaler may be prior-loaded with at least one dose of the compositions of the present invention. Typically, the metered dose inhaler will be prior-loaded with a plurality of doses. In certain other embodiments, the metered dose inhaler is packaged separately from the composition, with a plurality of doses typically present within a cartridge dimensioned to engage within the metered dose inhaler.

In embodiments comprising a dry powder inhaler, the metered dose inhaler may be prior loaded with one or more doses of dry composition, or in other embodiments is separately packaged from one or more dry powder doses.

Various embodiments of the kits of the present invention further comprise a set of instructions for use of the included composition. The instructions may inform the user of methods for administration of the composition of the invention, suggested dosages and schedules for various levels of exposure to environmental conditions that promote COPD or emphysema, such as smoking or air pollution, precautions, expected results, warnings concerning improper use, and the like. The instructions may be in any form, and provided, e.g., as a separate insert or on a label that is affixed to the container or packaging. Instructions include instructions for any of the methods described herein.

In some embodiments, instructions are directed to the use of AAT by inhalation in the prevention or treatment of COPD or emphysema. In some embodiments, instructions are directed to the use of AAT by inhalation in the prevention or treatment of COPD. In some embodiments, instructions are directed to the use of AAT by inhalation in the prevention or treatment of emphysema.

In some embodiments, the kits further include one or more additional agents, above-described, for treatment of COPD, including one or more bronchodilator, one or more corticosteroid, and/or one or more mucolytics, expectorants, antibiotic.

In another aspect, the invention provides a cigarette filter, the cigarette filter configured to deliver AAT, or a functionally active portion or fusion thereof, by inhalation during smoking. Cigarette filters for delivery of medicaments are known. See U.S. Pat. Nos. 6,789,546; 6,145,511; 5,472,002, the disclosures of which are incorporated herein by reference in their entireties.

In various embodiments, AAT is uniformly impregnated within the filter. In other embodiments, AAT is nonuniformly present, contained in one or more segregated vacuoles, chambers, beads, or other concentrated repositories.

In various embodiments, the AAT protein is any of the above-described AAT proteins, functionally active portions, or fusions above-described. In one series of embodiments, the AAT protein is recombinant. In some embodiments, the recombinant AAT is unglycosylated. In some of these latter embodiments, the unglycosylated recombinant AAT is rAAT.

The filter may be physically separate from a cigarette, the cigarette containing legally-consumable combustible material, such as tobacco, and engageable thereto, or may be integral to a cigarette containing the combustible material.

AAT is included in the filter in an amount sufficient to deliver an effective dose during smoking, as above-described.

In yet another aspect, the invention provides a composition, the composition comprising tobacco and AAT. The composition may be fashioned as a cigarette.

In various embodiments, the AAT protein is any of the above-described AAT proteins, functionally active portions, or fusions above-described. In one series of embodiments, the AAT protein is recombinant. In some embodiments, the recombinant AAT protein is unglycosylated. In some of these latter embodiments, the unglycosylated recombinant AAT is rAAT.

The present invention is further illustrated by the following example, presented by way of illustration and not limitation.

EXAMPLE 1

This example shows the efficacy of AAT administered by pulmonary delivery in the prevention of indices of emphysema in an established model, the murine model of cigarette smoke-related emphysema.

Treatment Groups:

Five groups of adult mice (12 weeks of age at initiation) were studied.

Group 1 animals (32 animals) were control nonsmoking animals.

Animals in groups 2-5 were exposed to two cigarettes per day, 6 days/wk for 6 months.

Group 2 animals (32 animals) were administered aerosolized vehicle buffer (10 mM NaCl, 20 mM sodium phosphate, 5 mM N-acetyl cysteine, 1 mM sodium citrate, pH 7.4; 10 ml/5 animals) followed by cigarette smoke.

Group 3 animals (32 animals) received low dose aerosolized rAAT (1.15 mg/ml in vehicle buffer; 10 ml/5 animals; dose 1) and then smoked.

Group 4 animals (32 animals) received mid-dose aerosolized AAT (5.75 mg/ml in vehicle buffer; 10 ml/5 animals; dose 2) and then smoked.

Group 5 animals (32 animals) were administered high-dose aerosolized AAT (11.5 mg/ml in vehicle buffer; 10 ml/5 animals; dose 3) for 30 minutes and then smoked.

To deliver vehicle (group 2) or drug, the animals (five at a time) were placed in the drug delivery device, which delivered five separate, equal doses of AAT, one to each mouse, as an aerosolized liquid. Ten (10) mL of sterile saline or drug was placed in the nebulizer and delivered to each group of five animals. Delivery proceeded until the nebulizer ran dry (about 30 minutes).

The nebulizer (Aerogen, Inc., Mountain View, Calif.) produced particles of 3-4 μm MMAD, with 90% efficiency. An estimated 6% of nebulized drug is delivered to the animals' breathing zone, with about 5% of drug in the breathing zone estimated to be deposited in the deep lung, for an overall estimated efficiency of 0.27%.

Within each treatment group there were three time points for analysis: 1 week, 3 months, and 6 months. After one week, 3 months, and 6 months on study, 10 animals, 10 animals, and 12 animals respectively, from each group were sacrificed and analytical work on lungs and lung samples was performed (see below).

Analyses:

In each animal, the right lung was removed and used for fixation/inflation and paraffin embedding to study morphometry, to determine mean linear intercept ($L_m$), which is the distance between the walls of alveoli, and which increases as proteases (e.g., elastase) break down pulmonary structure.

The left lung was subjected to bronchoalveolar lavage (BAL) to determine levels of the inflammatory cell types, macrophages and neutrophils, which were counted by morphology. BAL samples were collected using 0.5 mL rinses of the left lung.

Results

The following table (Table 5) summarizes the results for $L_m$ (as percent reduction in enlargement compared to untreated smokers), macrophages, and neutrophils in lungs of treated and nontreated animals at the six-month timepoint.

TABLE 5

| Group | Lm (P value vs. smoker) | Macrophages, cell count/ml BAL fluid | Neutrophils, cell count/ml BAL fluid |
|---|---|---|---|
| Non-smokers | 100 (0.01) | 35,720 | 924 |
| Smokers | 0 (—) | 48,538 | 2012 |
| AAT, dose 1 | 70 (0.02) | 38,398 | 698 |
| AAT, dose 2 | 73 (0.01) | 43,367 | 832 |
| AAT, dose 3 | 43 (0.08) | 42,073 | 1638 |

The following table (Table 6) summarizes the results for assays of matrix metalloprotease 9 (MMP9) activity.

TABLE 6

| Treatment | # of animals possessing MMP9 activity | Average Activity (mAU/min ± SD) |
|---|---|---|
| Non-smokers | 2/10 | 0.38 ± 0.16 |
| Vehicle smoker | 4/10 | 0.57 ± 0.32 |
| 1.15 mg rAAT/mL | 1/10 | 0.69 |
| 5.75 mg rAAT/mL | 3/10 | 0.56 ± 0.18 |
| 11.5 mg rAAT/mL | 5/9 | 0.78 ± 0.49 |

This Example demonstrates significant reduction of indices of emphysema by inhalation of AAT in animals chronically exposed to cigarette smoke, an established cause of emphysema.

In particular, the data demonstrate that aerosolized rAAT retains biological activity even in the setting of chronic exposure to cigarette smoke. The data also demonstrate that inhaled rAAT can normalize smoke-induced inflammatory cell influx and ameliorate air-space enlargement. Low μg quantities of rAAT delivered to the alveoli are sufficient to significantly inhibit air-space enlargement. Surprisingly, more inhaled rAAT is not better in these experiments. Findings confirm that neutrophil elastase is a key protease responsible for smoke-induced lung damage.

The data further suggest that targeted delivery of rAAT via inhalation in ex-smokers with progressive emphysema could circumvent any systemic safety issues and reduce drug requirements.

All publications, patents and patent applications cited herein are hereby incorporated by reference in their entirety for all purposes to the same extent as if each individual publication, patent or patent application were specifically and individually indicated to be so incorporated by reference.

As used herein, the singular form of the indefinite and definite articles "a" "an", and "the" includes plural references, unless explicitly indicated otherwise. For example, "a symptom" means one or more symptoms.

It is understood that the example and embodiments described herein are for illustrative purposes only and that various modifications or changes in light thereof will be suggested to persons skilled in the art and are to be included within the spirit and purview of this application and scope of the appended claims.

The invention claimed is:

1. A method of treating chronic obstructive pulmonary disease (COPD), the method comprising: administering a dry powder composition substantially free of carbohydrate comprising an effective amount of unglycosylated alpha 1-antitrypsin (AAT), or functionally active portion thereof, by inhalation to the lungs of an individual having COPD, wherein the AAT is effective against the progression of COPD, and wherein the dry powder composition has less than 0.1% carbohydrate based on a weight percentage.

2. A method of preventing indicia of chronic obstructive pulmonary disease (COPD), the method comprising: administering a dry powder composition substantially free of carbohydrate comprising an effective amount of unglycosylated alpha 1-antitrypsin (AAT), or functionally active portion thereof, by inhalation to the lungs of an individual at risk of COPD, wherein the AAT is effective against the development of the indicia of COPD, and wherein the dry powder composition has less than 0.1% carbohydrate based on a weight percentage.

3. The method of claim 1 or 2, wherein the unglycosylated AAT is recombinant AAT.

4. The method of claim 3, wherein the recombinant AAT is produced in yeast.

5. The method of claim 1 or 2, wherein the dry powder composition further comprises a halide salt.

6. The method of claim 5, wherein the halide salt is present at a level of at least or about 10 micromoles per 100 mg AAT.

7. The method of claim 5, wherein the halide salt is present at a level of at least or about 50 micromoles per 100 mg AAT.

8. The method of claim 5, wherein the halide salt is present at a level of at least or about 100 micromoles per 100 mg AAT.

9. The method of claim 5, wherein the halide salt is a chloride salt.

10. The method of claim 9, wherein the chloride salt is NaCl.

11. The method of claim 1 or 2, wherein the lungs of said individual are periodically exposed to at least one airborne agent capable of oxidizing AAT.

12. The method of claim 11, wherein said individual is periodically exposed to tobacco smoke.

13. The method of claim 12 wherein the individual is a smoker.

14. The method of claim 1 or 2 wherein the individual is a former smoker.

* * * * *

SEQUENCE LISTING

<160> NUMBER OF SEQ ID NOS: 33

<210> SEQ ID NO 1
<211> LENGTH: 1182
<212> TYPE: DNA
<213> ORGANISM: Homo sapiens

<400> SEQUENCE: 1

```
gaagaccctc aaggcgacgc cgctcaaaaa accgacacca gtcatcacga ccaagaccat    60
ccgactttta ataaaattac tccaaattta gccgaatttg cttttctttt gtatagacaa   120
ttagctcatc aaagtaattc tactaacatt ttttttagtc ctgtttctat tgccactgct   180
ttcgccatgt tgagtttagg tactaaagcc gatacccatg acgagatttt agaaggttta   240
aactttaatt tgaccgaaat cccagaagcc caaattcacg agggttttca agagttgttg   300
agaactttga atcaacctga ttctcaattg caattaacta ctggtaacgg tttattttg   360 tctgaaggtt taaaattggt tgacaaattc ctagaagacg tcaagaaact atatcatagt   420
gaggctttta ccgttaattt tggtgatact gaggaagcta aaaagcaaat taatgattat   480
gttgagaaag gcacccaggg taagatcgtt gacctagtta agaattaga tcgtgatacc   540 gtcttcgcac tagttaacta tattttttc aagggtaagt gggaacgtcc tttcgaggtt   600
aaagatactg aagaggaaga ttttcatgtt gatcaagtta ctactgtcaa agttccaatg   660
atgaaaagac tgggtatgtt caatattcaa cattgcaaaa aattaagttc ttgggtctta   720
ttaatgaagt atttaggtaa cgctactgct attttttttt taccagacga aggtaagctt   780
caacatttag agaatgagtt gactcatgac attattacta aatttttaga gaacgaggat   840
cgtcgtagcg cttctctgca cctgccaaag ttaagtatca ccggtactta cgacttaaaa   900
tctgttttag gccagttagg tattaccaaa gttttttcta acggtgccga tttgagtggt   960
gttactgaag aagctccatt aaaattgagt aaagctgttc acaaagccgt cttaactatt  1020
gatgaaaagg gtaccgaggc cgccggcgct atgttcctgg aagctattcc aatgagcatt  1080
ccaccagaag ttaaatttaa taaaccattc gttttttctga tgatcgagca gaacactaaa  1140
```
agcccattgt ttatgggtaa ggttgtcaac ccaactcaga ag            1182

<210> SEQ ID NO 2
<211> LENGTH: 394
<212> TYPE: PRT
<213> ORGANISM: Homo sapiens

<400> SEQUENCE: 2

```
Glu Asp Pro Gln Gly Asp Ala Ala Gln Lys Thr Asp Thr Ser His His
 1               5                  10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
           100                 105                 110

Thr Thr Gly Asn Gly Leu Phe Leu Ser Glu Gly Leu Lys Leu Val Asp
       115                 120                 125

Lys Phe Leu Glu Asp Val Lys Lys Leu Tyr His Ser Glu Ala Phe Thr
   130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
```

```
                370             375             380
Met Gly Lys Val Val Asn Pro Thr Gln Lys
385                 390

<210> SEQ ID NO 3
<211> LENGTH: 321
<212> TYPE: DNA
<213> ORGANISM: Homo sapiens

<400> SEQUENCE: 3
tctggaaagt ctttcaaggc cggtgtttgt ccaccaaaga agtccgctca atgtttgaga    60
tacaagaagc cagaatgtca atccgactgg caatgtccag gtaagaagag atgttgtcca   120
gacacttgtg gtatcaagtg tctagaccca gttgacaccc caaacccaac tagaagaaag   180
ccaggtaagt gtccagttac ttacggtcaa tgtttgatgt tgaacccacc aaacttctgt   240
gaaatggacg gtcaatgtaa gagagacttg aagtgttgta tgggtatgtg tggtaagtcc   300
tgtgtttccc cagtcaaggc c                                            321

<210> SEQ ID NO 4
<211> LENGTH: 107
<212> TYPE: PRT
<213> ORGANISM: Homo sapiens

<400> SEQUENCE: 4

Ser Gly Lys Ser Phe Lys Ala Gly Val Cys Pro Pro Lys Lys Ser Ala
 1               5                  10                  15

Gln Cys Leu Arg Tyr Lys Lys Pro Glu Cys Gln Ser Asp Trp Gln Cys
            20                  25                  30

Pro Gly Lys Lys Arg Cys Cys Pro Asp Thr Cys Gly Ile Lys Cys Leu
        35                  40                  45

Asp Pro Val Asp Thr Pro Asn Pro Thr Arg Arg Lys Pro Gly Lys Cys
    50                  55                  60

Pro Val Thr Tyr Gly Gln Cys Leu Met Leu Asn Pro Pro Asn Phe Cys
65                  70                  75                  80

Glu Met Asp Gly Gln Cys Lys Arg Asp Leu Lys Cys Cys Met Gly Met
                85                  90                  95

Cys Gly Lys Ser Cys Val Ser Pro Val Lys Ala
            100                 105

<210> SEQ ID NO 5
<211> LENGTH: 552
<212> TYPE: DNA
<213> ORGANISM: Homo sapiens

<400> SEQUENCE: 5
tgcacctgtg tcccacccca cccacagacg gccttctgca attccgacct cgtcatcagg    60
gccaagttcg tggggacacc agaagtcaac cagaccacct tataccagcg ttatgagatc   120
aagatgacca agatgtataa agggttccaa gccttagggg atgccgctga catccggttc   180
gtctacaccc ccgccatgga gagtgtctgc ggatacttcc acaggtccca caaccgcagc   240
gaggagtttc tcattgctgg aaaactgcag gatggactct tgcacatcac tacctgcagt   300
ttcgtggctc cctggaacag cctgagctta gctcagcgcc ggggcttcac caagacctac   360
actgttggct gtgaggaatg cacagtgttt ccctgtttat ccatcccctg caaactgcag   420
agtggcactc attgcttgtg gacggaccag ctcctccaag gctctgaaaa gggcttccag   480
tcccgtcacc ttgcctgcct gcctcgggag ccagggctgt gcacctggca gtccctgcgg   540
```

-continued tcccagatag cc                                                                552

<210> SEQ ID NO 6
<211> LENGTH: 184
<212> TYPE: PRT
<213> ORGANISM: Homo sapiens

<400> SEQUENCE: 6

Cys Thr Cys Val Pro Pro His Pro Gln Thr Ala Phe Cys Asn Ser Asp
 1               5                  10                  15

Leu Val Ile Arg Ala Lys Phe Val Gly Thr Pro Glu Val Asn Gln Thr
            20                  25                  30

Thr Leu Tyr Gln Arg Tyr Glu Ile Lys Met Thr Lys Met Tyr Lys Gly
        35                  40                  45

Phe Gln Ala Leu Gly Asp Ala Asp Ile Arg Phe Val Tyr Thr Pro
    50                  55                  60

Ala Met Glu Ser Val Cys Gly Tyr Phe His Arg Ser His Asn Arg Ser
65                  70                  75                  80

Glu Glu Phe Leu Ile Ala Gly Lys Leu Gln Asp Gly Leu Leu His Ile
                85                  90                  95

Thr Thr Cys Ser Phe Val Ala Pro Trp Asn Ser Leu Ser Leu Ala Gln
            100                 105                 110

Arg Arg Gly Phe Thr Lys Thr Tyr Thr Val Gly Cys Glu Glu Cys Thr
        115                 120                 125

Val Phe Pro Cys Leu Ser Ile Pro Cys Lys Leu Gln Ser Gly Thr His
    130                 135                 140

Cys Leu Trp Thr Asp Gln Leu Leu Gln Gly Ser Glu Lys Gly Phe Gln
145                 150                 155                 160

Ser Arg His Leu Ala Cys Leu Pro Arg Glu Pro Gly Leu Cys Thr Trp
                165                 170                 175

Gln Ser Leu Arg Ser Gln Ile Ala
            180

<210> SEQ ID NO 7
<211> LENGTH: 1525
<212> TYPE: DNA
<213> ORGANISM: Homo sapiens

<400> SEQUENCE: 7
tctagaccat gtctggaaag tctttcaagg ccggtgtttg tccaccaaag aagtccgctc     60
aatgtttgag atacaagaag ccagaatgtc aatccgactg caatgtccaa ggtaagaaga   120
gatgttgtcc agacacttgt ggtatcaagt gtctagaccc agttgacacc ccaaacccaa   180
ctagaagaaa gccaggtaag tgtccagtta cttacggtca atgtttgatg ttgaacccac   240
caaacttctg tgaaatggac ggtcaatgta agagagactt gaagtgttgt atgggtatgt   300
gtggtaagtc ctgtgtttcc ccagtcaagg ccatggaaga ccctcaaggc gacgccgctc   360
aaaaaaccga caccagtcat cacgaccaag accatccgac ttttaataaa attactccaa   420
atttagccga atttgctttt tctttgtata gacaattagc tcatcaaagt aattctacta   480 acatttttt tagtcctgtt tctattgcca ctgctttcgc catgttgagt ttaggtacta   540
aagccgatac ccatgacgag attttagaag gtttaaactt taatttgacc gaaatcccag   600
aagcccaaat tcacgagggt tttcaagagt tgttgagaac tttgaatcaa cctgattctc   660
aattgcaatt aactactggt aacggttat ttttgtctga aggtttaaaa ttggttgaca   720
aattcctaga agacgtcaag aaactatatc atagtgaggc ttttaccgtt aattttggtg   780

```
atactgagga agctaaaaag caaattaatg attatgttga gaaaggcacc cagggtaaga    840
tcgttgacct agttaaagaa ttagatcgtg ataccgtctt cgcactagtt aactatattt    900
ttttcaaggg taagtgggaa cgtcctttcg aggttaaaga tactgaagag gaagattttc    960
atgttgatca agttactact gtcaaagttc caatgatgaa aagactgggt atgttcaata   1020
ttcaacattg caaaaaatta agttcttggg tcttattaat gaagtattta ggtaacgcta   1080
ctgctatttt tttttttacca gacgaaggta agcttcaaca tttagagaat gagttgactc   1140
atgacattat tactaaattt ttagagaacg aggatcgtcg tagcgcttct ctgcacctgc   1200
caaagttaag tatcaccggt acttacgact aaaatctgt tttaggccag ttaggtatta   1260
ccaaagtttt ttctaacggt gccgatttga gtggtgttac tgaagaagct ccattaaaat   1320
tgagtaaagc tgttcacaaa gccgtcttaa ctattgatga aaagggtacc gaggccgccg   1380
gcgctatgtt cctggaagct attccaatga gcattccacc agaagttaaa tttaataaac   1440
cattcgtttt tctgatgatc gagcagaaca ctaaaagccc attgtttatg ggtaaggttg   1500
tcaacccaac tcagaagtag tcgac                                          1525

<210> SEQ ID NO 8
<211> LENGTH: 503
<212> TYPE: PRT
<213> ORGANISM: Homo sapiens

<400> SEQUENCE: 8

Met Ser Gly Lys Ser Phe Lys Ala Gly Val Cys Pro Pro Lys Lys Ser
 1               5                  10                  15

Ala Gln Cys Leu Arg Tyr Lys Lys Pro Glu Cys Gln Ser Asp Trp Gln
             20                  25                  30

Cys Pro Gly Lys Lys Arg Cys Cys Pro Asp Thr Cys Gly Ile Lys Cys
         35                  40                  45

Leu Asp Pro Val Asp Thr Pro Asn Pro Thr Arg Arg Lys Pro Gly Lys
     50                  55                  60

Cys Pro Val Thr Tyr Gly Gln Cys Leu Met Leu Asn Pro Pro Asn Phe
 65                  70                  75                  80

Cys Glu Met Asp Gly Gln Cys Lys Arg Asp Leu Lys Cys Cys Met Gly
                 85                  90                  95

Met Cys Gly Lys Ser Cys Val Ser Pro Val Lys Ala Met Glu Asp Pro
            100                 105                 110

Gln Gly Asp Ala Ala Gln Lys Thr Asp Thr Ser His His Asp Gln Asp
        115                 120                 125

His Pro Thr Phe Asn Lys Ile Thr Pro Asn Leu Ala Glu Phe Ala Phe
    130                 135                 140

Ser Leu Tyr Arg Gln Leu Ala His Gln Ser Asn Ser Thr Asn Ile Phe
145                 150                 155                 160

Phe Ser Pro Val Ser Ile Ala Thr Ala Phe Ala Met Leu Ser Leu Gly
                165                 170                 175

Thr Lys Ala Asp Thr His Asp Glu Ile Leu Glu Gly Leu Asn Phe Asn
            180                 185                 190

Leu Thr Glu Ile Pro Glu Ala Gln Ile His Glu Gly Phe Gln Glu Leu
        195                 200                 205

Leu Arg Thr Leu Asn Gln Pro Asp Ser Gln Leu Gln Leu Thr Thr Gly
    210                 215                 220

Asn Gly Leu Phe Leu Ser Glu Gly Leu Lys Leu Val Asp Lys Phe Leu
225                 230                 235                 240

Glu Asp Val Lys Lys Leu Tyr His Ser Glu Ala Phe Thr Val Asn Phe
```

```
                        245                 250                 255
Gly Asp Thr Glu Glu Ala Lys Lys Gln Ile Asn Asp Tyr Val Glu Lys
                260                 265                 270
Gly Thr Gln Gly Lys Ile Val Asp Leu Val Lys Glu Leu Asp Arg Asp
            275                 280                 285
Thr Val Phe Ala Leu Val Asn Tyr Ile Phe Phe Lys Gly Lys Trp Glu
        290                 295                 300
Arg Pro Phe Glu Val Lys Asp Thr Glu Glu Asp Phe His Val Asp
305                 310                 315                 320
Gln Val Thr Thr Val Lys Val Pro Met Met Lys Arg Leu Gly Met Phe
                325                 330                 335
Asn Ile Gln His Cys Lys Lys Leu Ser Ser Trp Val Leu Leu Met Lys
                340                 345                 350
Tyr Leu Gly Asn Ala Thr Ala Ile Phe Phe Leu Pro Asp Glu Gly Lys
            355                 360                 365
Leu Gln His Leu Glu Asn Glu Leu Thr His Asp Ile Ile Thr Lys Phe
        370                 375                 380
Leu Glu Asn Glu Asp Arg Arg Ser Ala Ser Leu His Leu Pro Lys Leu
385                 390                 395                 400
Ser Ile Thr Gly Thr Tyr Asp Leu Lys Ser Val Leu Gly Gln Leu Gly
                405                 410                 415
Ile Thr Lys Val Phe Ser Asn Gly Ala Asp Leu Ser Gly Val Thr Glu
                420                 425                 430
Glu Ala Pro Leu Lys Leu Ser Lys Ala Val His Lys Ala Val Leu Thr
            435                 440                 445
Ile Asp Glu Lys Gly Thr Glu Ala Ala Gly Ala Met Phe Leu Glu Ala
        450                 455                 460
Ile Pro Met Ser Ile Pro Pro Glu Val Lys Phe Asn Lys Pro Phe Val
465                 470                 475                 480
Phe Leu Met Ile Glu Gln Asn Thr Lys Ser Pro Leu Phe Met Gly Lys
                485                 490                 495
Val Val Asn Pro Thr Gln Lys
            500

<210> SEQ ID NO 9
<211> LENGTH: 1756
<212> TYPE: DNA
<213> ORGANISM: Homo sapiens

<400> SEQUENCE: 9
tctagaccat gtgcacctgt gtcccacccc acccacagac ggccttctgc aattccgacc    60
tcgtcatcag ggccaagttc gtggggacac agaagtcaa ccagaccacc ttataccagc    120
gttatgagat caagatgacc aagatgtata aagggttcca agccttaggg gatgccgctg    180
acatccggtt cgtctacacc cccgccatgg agagtgtctg cggatacttc acaggtccc    240 acaaccgcag cgaggagttt ctcattgctg aaaaactgca ggatggactc ttgcacatca    300
ctacctgcag tttcgtggct ccctggaaca gcctgagctt agctcagcgc cggggcttca    360
ccaagaccta cactgttggc tgtgaggaat gcacagtgtt ccctgtttta tccatcccct    420
gcaaactgca gagtggcact cattgcttgt ggacggacca gctcctccaa ggctctgaaa    480
agggcttcca gtcccgtcac cttgcctgcc tgcctcggga gccagggctg tgcacctggc    540
agtccctgcg gtcccagata gccatggaag accctcaagg cgacgccgct caaaaaaccg    600
acaccagtca tcacgaccaa gaccatccga ctttaataa aattactcca aatttagccg    660
```

```
aatttgcttt ttctttgtat agacaattag ctcatcaaag taattctact aacattttt    720 ttagtcctgt ttctattgcc actgctttcg ccatgttgag tttaggtact aaagccgata    780
cccatgacga gattttagaa ggtttaaact taatttgac cgaaatccca gaagcccaaa    840
ttcacgaggg ttttcaagag ttgttgagaa ctttgaatca acctgattct caattgcaat    900
taactactgg taacggttta ttttgtctg aaggtttaaa attggttgac aaattcctag    960
aagacgtcaa gaaactatat catagtgagg cttttaccgt taattttggt gatactgagg   1020
aagctaaaaa gcaaattaat gattatgttg agaaaggcac ccagggtaag atcgttgacc   1080
tagttaaaga attagatcgt gataccgtct tcgcactagt taactatatt tttttcaagg   1140
gtaagtggga acgtcctttc gaggttaaag atactgaaga ggaagatttt catgttgatc   1200
aagttactac tgtcaaagtt ccaatgatga aaagactggg tatgttcaat attcaacatt   1260
gcaaaaaatt aagttcttgg gtcttattaa tgaagtattt aggtaacgct actgctatt    1320 ttttttttacc agacgaaggt aagcttcaac atttagagaa tgagttgact catgacatta   1380
ttactaaatt tttagagaac gaggatcgtc gtagcgcttc tctgcacctg ccaaagttaa   1440
gtatcaccgg tacttacgac ttaaaatctg ttttaggcca gttaggtatt accaaagttt   1500
tttctaacgg tgccgatttg agtggtgtta ctgaagaagc tccattaaaa ttgagtaaag   1560
ctgttcacaa agccgtctta actattgatg aaaagggtac cgaggccgcc ggcgctatgt   1620
tcctggaagc tattccaatg agcattccac cagaagttaa atttaataaa ccattcgttt   1680
ttctgatgat cgagcagaac actaaaagcc cattgtttat gggtaaggtt gtcaacccaa   1740
ctcagaagta gtcgac                                                   1756
```

<210> SEQ ID NO 10
<211> LENGTH: 580
<212> TYPE: PRT
<213> ORGANISM: Homo sapiens

<400> SEQUENCE: 10

```
Met Cys Thr Cys Val Pro Pro His Pro Gln Thr Ala Phe Cys Asn Ser
1               5                   10                  15

Asp Leu Val Ile Arg Ala Lys Phe Val Gly Thr Pro Glu Val Asn Gln
            20                  25                  30

Thr Thr Leu Tyr Gln Arg Tyr Glu Ile Lys Met Thr Lys Met Tyr Lys
        35                  40                  45

Gly Phe Gln Ala Leu Gly Asp Ala Ala Asp Ile Arg Phe Val Tyr Thr
    50                  55                  60

Pro Ala Met Glu Ser Val Cys Gly Tyr Phe His Arg Ser His Asn Arg
65                  70                  75                  80

Ser Glu Glu Phe Leu Ile Ala Gly Lys Leu Gln Asp Gly Leu Leu His
                85                  90                  95

Ile Thr Thr Cys Ser Phe Val Ala Pro Trp Asn Ser Leu Ser Leu Ala
            100                 105                 110

Gln Arg Arg Gly Phe Thr Lys Thr Tyr Thr Val Gly Cys Glu Glu Cys
        115                 120                 125

Thr Val Phe Pro Cys Leu Ser Ile Pro Cys Lys Leu Gln Ser Gly Thr
    130                 135                 140

His Cys Leu Trp Thr Asp Gln Leu Leu Gln Gly Ser Glu Lys Gly Phe
145                 150                 155                 160

Gln Ser Arg His Leu Ala Cys Leu Pro Arg Glu Pro Gly Leu Cys Thr
                165                 170                 175

Trp Gln Ser Leu Arg Ser Gln Ile Ala Met Glu Asp Pro Gln Gly Asp
```

```
                   180             185             190
Ala Ala Gln Lys Thr Asp Thr Ser His His Asp Gln Asp His Pro Thr
            195                 200             205
Phe Asn Lys Ile Thr Pro Asn Leu Ala Glu Phe Ala Phe Ser Leu Tyr
            210                 215             220
Arg Gln Leu Ala His Gln Ser Asn Ser Thr Asn Ile Phe Phe Ser Pro
225                 230                 235                 240
Val Ser Ile Ala Thr Ala Phe Ala Met Leu Ser Leu Gly Thr Lys Ala
                245                 250                 255
Asp Thr His Asp Glu Ile Leu Glu Gly Leu Asn Phe Asn Leu Thr Glu
                260                 265                 270
Ile Pro Glu Ala Gln Ile His Glu Gly Phe Gln Glu Leu Leu Arg Thr
                275                 280                 285
Leu Asn Gln Pro Asp Ser Gln Leu Gln Leu Thr Thr Gly Asn Gly Leu
            290                 295                 300
Phe Leu Ser Glu Gly Leu Lys Leu Val Asp Lys Phe Leu Glu Asp Val
305                 310                 315                 320
Lys Lys Leu Tyr His Ser Glu Ala Phe Thr Val Asn Phe Gly Asp Thr
                    325                 330                 335
Glu Glu Ala Lys Lys Gln Ile Asn Asp Tyr Val Glu Lys Gly Thr Gln
                340                 345                 350
Gly Lys Ile Val Asp Leu Val Lys Glu Leu Asp Arg Asp Thr Val Phe
                355                 360                 365
Ala Leu Val Asn Tyr Ile Phe Phe Lys Gly Lys Trp Glu Arg Pro Phe
            370                 375                 380
Glu Val Lys Asp Thr Glu Glu Glu Asp Phe His Val Asp Gln Val Thr
385                 390                 395                 400
Thr Val Lys Val Pro Met Met Lys Arg Leu Gly Met Phe Asn Ile Gln
                    405                 410                 415
His Cys Lys Lys Leu Ser Ser Trp Val Leu Leu Met Lys Tyr Leu Gly
                420                 425                 430
Asn Ala Thr Ala Ile Phe Phe Leu Pro Asp Glu Gly Lys Leu Gln His
                435                 440                 445
Leu Glu Asn Glu Leu Thr His Asp Ile Ile Thr Lys Phe Leu Glu Asn
450                 455                 460
Glu Asp Arg Arg Ser Ala Ser Leu His Leu Pro Lys Leu Ser Ile Thr
465                 470                 475                 480
Gly Thr Tyr Asp Leu Lys Ser Val Leu Gly Gln Leu Gly Ile Thr Lys
                    485                 490                 495
Val Phe Ser Asn Gly Ala Asp Leu Ser Gly Val Thr Glu Glu Ala Pro
                500                 505                 510
Leu Lys Leu Ser Lys Ala Val His Lys Ala Val Leu Thr Ile Asp Glu
            515                 520                 525
Lys Gly Thr Glu Ala Ala Gly Ala Met Phe Leu Glu Ala Ile Pro Met
            530                 535                 540
Ser Ile Pro Pro Glu Val Lys Phe Asn Lys Pro Phe Val Phe Leu Met
545                 550                 555                 560
Ile Glu Gln Asn Thr Lys Ser Pro Leu Phe Met Gly Lys Val Val Asn
                    565                 570                 575
Pro Thr Gln Lys
            580

<210> SEQ ID NO 11
<211> LENGTH: 5
```

```
<212> TYPE: PRT
<213> ORGANISM: Homo sapiens

<400> SEQUENCE: 11

Gln Val Val Ala Gly
 1               5

<210> SEQ ID NO 12
<211> LENGTH: 5
<212> TYPE: PRT
<213> ORGANISM: Bacteria (streptomyces)
<220> FEATURE:
<221> NAME/KEY: MOD_RES
<222> LOCATION: 1
<223> OTHER INFORMATION: Xaa= valine modified with N-terminal isovaleryl
      group
<220> FEATURE:
<221> NAME/KEY: MOD_RES
<222> LOCATION: 3, 5
<223> OTHER INFORMATION: Xaa= statin

<400> SEQUENCE: 12

Xaa Val Xaa Ala Xaa
 1               5

<210> SEQ ID NO 13
<211> LENGTH: 1582
<212> TYPE: DNA
<213> ORGANISM: Homo sapiens

<400> SEQUENCE: 13
tctagaccat gtgcacctgt gtcccacccc acccacagac ggccttctgc aattccgacc      60
tcgtcatcag ggccaagttc gtggggacac cagaagtcaa ccagaccacc ttataccagc     120
gttatgagat caagatgacc aagatgtata agggttcca agcctttaggg gatgccgctg     180 acatccggtt cgtctacacc cccgccatgg agagtgtctg cggatacttc cacaggtccc     240
acaaccgcag cgaggagttt ctcattgctg aaaaactgca ggatggactc ttgcacatca     300
ctacctgcag tttcgtggct ccctggaaca gcctgagctt agctcagcgc cggggcttca     360
ccaagacgta tactgttggc tgtgaggaaa tggaagaccc tcaaggcgac gccgctcaaa     420
aaaccgacac cagtcatcac gaccaagacc atccgacttt taataaaatt actccaaatt     480
tagccgaatt tgcttttttct tgtatagac aattagctca tcaaagtaat tctactaaca     540 tttttttttag tcctgtttct attgccactg cttttcgccat gttgagttta ggtactaaag     600
ccgataccca tgacgagatt ttagaaggtt taaactttaa tttgaccgaa atcccagaag     660
cccaaattca cgagggtttt caagagttgt tgagaacttt gaatcaacct gattctcaat     720
tgcaattaac tactggtaac ggtttatttt tgtctgaagg tttaaaattg gttgacaaat     780
tcctagaaga cgtcaagaaa ctatatcata gtgaggcttt taccgttaat tttggtgata     840
ctgaggaagc taaaaagcaa attaatgatt atgttgagaa aggcacccag gtaagatcg     900 ttgacctagt taagaattaa atcgtgata ccgtcttcgc actagttaac tatatttttt      960
tcaagggtaa gtgggaacgt cctttcgagg ttaaagatac tgaagaggaa gattttcatg    1020
ttgatcaagt tactactgtc aaagttccaa tgatgaaaag actgggtatg ttcaatattc    1080
aacattgcaa aaaattaagt tcttgggtct tattaatgaa gtatttaggt aacgctactg    1140
ctattttttt tttaccagac gaaggtaagc ttcaacattt agagaatgag ttgactcatg    1200
acattattac taaattttta gagaacgagg atcgtcgtag cgcttctctg cacctgccaa    1260
agttaagtat caccggtact tacgacttaa aatctgtttt aggccagtta ggtattacca    1320
```

-continued

```
aagttttttc taacggtgcc gatttgagtg gtgttactga agaagctcca ttaaaattga    1380
gtaaagctgt tcacaaagcc gtcttaacta ttgatgaaaa gggtaccgag ccgccggcg     1440 ctatgttcct ggaagctatt ccaatgagca ttccaccaga agttaaattt aataaaccat    1500 tcgttttct gatgatcgag cagaacacta aagcccatt gtttatgggt aaggttgtca     1560
acccaactca gaagtagtcg ac                                            1582
```

<210> SEQ ID NO 14
<211> LENGTH: 522
<212> TYPE: PRT
<213> ORGANISM: Homo sapiens

<400> SEQUENCE: 14

```
Met Cys Thr Cys Val Pro Pro His Pro Gln Thr Ala Phe Cys Asn Ser
  1               5                  10                  15

Asp Leu Val Ile Arg Ala Lys Phe Val Gly Thr Pro Glu Val Asn Gln
             20                  25                  30

Thr Thr Leu Tyr Gln Arg Tyr Glu Ile Lys Met Thr Lys Met Tyr Lys
         35                  40                  45

Gly Phe Gln Ala Leu Gly Asp Ala Ala Asp Ile Arg Phe Val Tyr Thr
     50                  55                  60

Pro Ala Met Glu Ser Val Cys Gly Tyr Phe His Arg Ser His Asn Arg
 65                  70                  75                  80

Ser Glu Glu Phe Leu Ile Ala Gly Lys Leu Gln Asp Gly Leu Leu His
                 85                  90                  95

Ile Thr Thr Cys Ser Phe Val Ala Pro Trp Asn Ser Leu Ser Leu Ala
            100                 105                 110

Gln Arg Arg Gly Phe Thr Lys Thr Tyr Thr Val Gly Cys Glu Glu Met
        115                 120                 125

Glu Asp Pro Gln Gly Asp Ala Ala Gln Lys Thr Asp Thr Ser His His
    130                 135                 140

Asp Gln Asp His Pro Thr Phe Asn Lys Ile Thr Pro Asn Leu Ala Glu
145                 150                 155                 160

Phe Ala Phe Ser Leu Tyr Arg Gln Leu Ala His Gln Ser Asn Ser Thr
                165                 170                 175

Asn Ile Phe Phe Ser Pro Val Ser Ile Ala Thr Ala Phe Ala Met Leu
            180                 185                 190

Ser Leu Gly Thr Lys Ala Asp Thr His Asp Glu Ile Leu Glu Gly Leu
        195                 200                 205

Asn Phe Asn Leu Thr Glu Ile Pro Glu Ala Gln Ile His Glu Gly Phe
    210                 215                 220

Gln Glu Leu Leu Arg Thr Leu Asn Gln Pro Asp Ser Gln Leu Gln Leu
225                 230                 235                 240

Thr Thr Gly Asn Gly Leu Phe Leu Ser Glu Gly Leu Lys Leu Val Asp
                245                 250                 255

Lys Phe Leu Glu Asp Val Lys Lys Leu Tyr His Ser Glu Ala Phe Thr
            260                 265                 270

Val Asn Phe Gly Asp Thr Glu Glu Ala Lys Lys Gln Ile Asn Asp Tyr
        275                 280                 285

Val Glu Lys Gly Thr Gln Gly Lys Ile Val Asp Leu Val Lys Glu Leu
    290                 295                 300

Asp Arg Asp Thr Val Phe Ala Leu Val Asn Tyr Ile Phe Phe Lys Gly
305                 310                 315                 320

Lys Trp Glu Arg Pro Phe Glu Val Lys Asp Thr Glu Glu Glu Asp Phe
                325                 330                 335
```

```
His Val Asp Gln Val Thr Thr Val Lys Val Pro Met Met Lys Arg Leu
            340                 345                 350
Gly Met Phe Asn Ile Gln His Cys Lys Lys Leu Ser Ser Trp Val Leu
        355                 360                 365
Leu Met Lys Tyr Leu Gly Asn Ala Thr Ala Ile Phe Phe Leu Pro Asp
    370                 375                 380
Glu Gly Lys Leu Gln His Leu Glu Asn Glu Leu Thr His Asp Ile Ile
385                 390                 395                 400
Thr Lys Phe Leu Glu Asn Glu Asp Arg Arg Ser Ala Ser Leu His Leu
            405                 410                 415
Pro Lys Leu Ser Ile Thr Gly Thr Tyr Asp Leu Lys Ser Val Leu Gly
        420                 425                 430
Gln Leu Gly Ile Thr Lys Val Phe Ser Asn Gly Ala Asp Leu Ser Gly
    435                 440                 445
Val Thr Glu Glu Ala Pro Leu Lys Leu Ser Lys Ala Val His Lys Ala
450                 455                 460
Val Leu Thr Ile Asp Glu Lys Gly Thr Glu Ala Ala Gly Ala Met Phe
465                 470                 475                 480
Leu Glu Ala Ile Pro Met Ser Ile Pro Pro Glu Val Lys Phe Asn Lys
            485                 490                 495
Pro Phe Val Phe Leu Met Ile Glu Gln Asn Thr Lys Ser Pro Leu Phe
        500                 505                 510
Met Gly Lys Val Val Asn Pro Thr Gln Lys
    515                 520

<210> SEQ ID NO 15
<211> LENGTH: 1525
<212> TYPE: DNA
<213> ORGANISM: Homo sapiens

<400> SEQUENCE: 15
tctagaccat ggaagaccct caaggcgacg ccgctcaaaa aaccgacacc agtcatcacg      60
accaagacca tccgactttt aataaaatta ctccaaattt agccgaattt gcttttctt     120 tgtatagaca attagctcat caaagtaatt ctactaacat ttttttagt cctgtttcta     180 ttgccactgc tttcgccatg ttgagtttag gtactaaagc cgatacccat gacgagattt     240
tagaaggttt aaactttaat ttgaccgaaa tcccagaagc ccaaattcac gagggttttc     300
aagagttgtt gagaactttg aatcaacctg attctcaatt gcaattaact actggtaacg     360
gtttattttt gtctgaaggt ttaaaattgg ttgacaaatt cctagaagac gtcaagaaac     420
tatatcatag tgaggctttt accgttaatt ttggtgatac tgaggaagct aaaaagcaaa     480
ttaatgatta tgttgagaaa ggcacccagg gtaagatcgt tgacctagtt aaagaattag     540
atcgtgatac cgtcttcgca ctagttaact atatttttt caagggtaag tgggaacgtc     600
ctttcgaggt taaagatact gaagaggaag attttcatgt tgatcaagtt actactgtca     660
aagttccaat gatgaaaaga ctgggtatgt tcaatattca acattgcaaa aaattaagtt     720
cttgggtctt attaatgaag tatttaggta acgctactgc tatttttttt ttaccagacg     780
aaggtaagct tcaacattta gagaatgagt tgactcatga cattattact aaattttag     840 agaacgagga tcgtcgtagc gcttctctgc acctgccaaa gttaagtatc accggtactt     900
acgacttaaa atctgtttta ggccagttag gtattaccaa agttttttct aacggtgccg     960
atttgagtgg tgttactgaa gaagctccat taaaattgag taaagctgtt cacaaagccg    1020
tcttaactat tgatgaaaag ggtaccgagg ccgccggcgc tatgttcctg gaagctattc    1080
```

-continued

```
caatgagcat tccaccagaa gttaaattta ataaaccatt cgttttctg atgatcgagc    1140 agaacactaa aagcccattg tttatgggta aggttgtcaa cccaactcag aagatgtccg    1200
gaaagtcttt caaggccggt gtttgtccac caaagaagtc cgctcaatgt ttgagataca    1260
agaagccaga atgtcaatcc gactggcaat gtccaggtaa gaagagatgt tgtccagaca    1320
cttgtggtat caagtgtcta gacccagttg acaccccaaa cccaactaga gaaaagccag    1380
gtaagtgtcc agttacttac ggtcaatgtt tgatgttgaa cccaccaaac ttctgtgaaa    1440
tggacggtca atgtaagaga gacttgaagt gttgtatggg tatgtgtggt aagtcctgtg    1500
tttccccagt caaggcctag tcgac                                          1525
```

<210> SEQ ID NO 16
<211> LENGTH: 503
<212> TYPE: PRT
<213> ORGANISM: Homo sapiens

<400> SEQUENCE: 16

```
Met Glu Asp Pro Gln Gly Asp Ala Ala Gln Lys Thr Asp Thr Ser His
  1               5                  10                  15

His Asp Gln Asp His Pro Thr Phe Asn Lys Ile Thr Pro Asn Leu Ala
             20                  25                  30

Glu Phe Ala Phe Ser Leu Tyr Arg Gln Leu Ala His Gln Ser Asn Ser
         35                  40                  45

Thr Asn Ile Phe Phe Ser Pro Val Ser Ile Ala Thr Ala Phe Ala Met
     50                  55                  60

Leu Ser Leu Gly Thr Lys Ala Asp Thr His Asp Glu Ile Leu Glu Gly
 65                  70                  75                  80

Leu Asn Phe Asn Leu Thr Glu Ile Pro Glu Ala Gln Ile His Glu Gly
                 85                  90                  95

Phe Gln Glu Leu Leu Arg Thr Leu Asn Gln Pro Asp Ser Gln Leu Gln
            100                 105                 110

Leu Thr Thr Gly Asn Gly Leu Phe Leu Ser Glu Gly Leu Lys Leu Val
        115                 120                 125

Asp Lys Phe Leu Glu Asp Val Lys Lys Leu Tyr His Ser Glu Ala Phe
    130                 135                 140

Thr Val Asn Phe Gly Asp Thr Glu Glu Ala Lys Lys Gln Ile Asn Asp
145                 150                 155                 160

Tyr Val Glu Lys Gly Thr Gln Gly Lys Ile Val Asp Leu Val Lys Glu
                165                 170                 175

Leu Asp Arg Asp Thr Val Phe Ala Leu Val Asn Tyr Ile Phe Phe Lys
            180                 185                 190

Gly Lys Trp Glu Arg Pro Phe Glu Val Lys Asp Thr Glu Glu Glu Asp
        195                 200                 205

Phe His Val Asp Gln Val Thr Thr Val Lys Val Pro Met Met Lys Arg
    210                 215                 220

Leu Gly Met Phe Asn Ile Gln His Cys Lys Lys Leu Ser Ser Trp Val
225                 230                 235                 240

Leu Leu Met Lys Tyr Leu Gly Asn Ala Thr Ala Ile Phe Phe Leu Pro
                245                 250                 255

Asp Glu Gly Lys Leu Gln His Leu Glu Asn Glu Leu Thr His Asp Ile
            260                 265                 270

Ile Thr Lys Phe Leu Glu Asn Glu Asp Arg Arg Ser Ala Ser Leu His
        275                 280                 285

Leu Pro Lys Leu Ser Ile Thr Gly Thr Tyr Asp Leu Lys Ser Val Leu
```

```
                    290                 295                 300
Gly Gln Leu Gly Ile Thr Lys Val Phe Ser Asn Gly Ala Asp Leu Ser
305                 310                 315                 320

Gly Val Thr Glu Glu Ala Pro Leu Lys Leu Ser Lys Ala Val His Lys
            325                 330                 335

Ala Val Leu Thr Ile Asp Glu Lys Gly Thr Glu Ala Ala Gly Ala Met
                340                 345                 350

Phe Leu Glu Ala Ile Pro Met Ser Ile Pro Pro Glu Val Lys Phe Asn
            355                 360                 365

Lys Pro Phe Val Phe Leu Met Ile Glu Gln Asn Thr Lys Ser Pro Leu
370                 375                 380

Phe Met Gly Lys Val Val Asn Pro Thr Gln Lys Met Ser Gly Lys Ser
385                 390                 395                 400

Phe Lys Ala Gly Val Cys Pro Pro Lys Lys Ser Ala Gln Cys Leu Arg
                405                 410                 415

Tyr Lys Lys Pro Glu Cys Gln Ser Asp Trp Gln Cys Pro Gly Lys Lys
            420                 425                 430

Arg Cys Cys Pro Asp Thr Cys Gly Ile Lys Cys Leu Asp Pro Val Asp
            435                 440                 445

Thr Pro Asn Pro Thr Arg Arg Lys Pro Gly Lys Cys Pro Val Thr Tyr
        450                 455                 460

Gly Gln Cys Leu Met Leu Asn Pro Pro Asn Phe Cys Glu Met Asp Gly
465                 470                 475                 480

Gln Cys Lys Arg Asp Leu Lys Cys Cys Met Gly Met Cys Gly Lys Ser
                485                 490                 495

Cys Val Ser Pro Val Lys Ala
            500

<210> SEQ ID NO 17
<211> LENGTH: 1756
<212> TYPE: DNA
<213> ORGANISM: Homo sapiens

<400> SEQUENCE: 17
tctagaccat ggaagaccct caaggcgacg ccgctcaaaa aaccgacacc agtcatcacg      60
accaagacca tccgactttt aataaaatta ctccaaattt agccgaattt gcttttctt    120 tgtatagaca attagctcat caaagtaatt ctactaacat ttttttttagt cctgtttcta   180 ttgccactgc tttcgccatg ttgagtttag gtactaaagc cgatacccat gacgagattt    240
tagaaggttt aaactttaat ttgaccgaaa tcccagaagc ccaaattcac gagggttttc    300
aagagttgtt gagaactttg aatcaacctg attctcaatt gcaattaact actggtaacg    360
gtttattttt gtctgaaggt ttaaaattgg ttgacaaatt cctagaagac gtcaagaaac    420
tatatcatag tgaggctttt accgttaatt ttggtgatac tgaggaagct aaaaagcaaa    480
ttaatgatta tgttgagaaa ggcacccagg gtaagatcgt tgacctagtt aaagaattag    540
atcgtgatac cgtcttcgca ctagttaact atatttttt caagggtaag tgggaacgtc     600
ctttcgaggt taaagatact gaagaggaag attttcatgt tgatcaagtt actactgtca    660
aagttccaat gatgaaaaga ctgggtatgt tcaatattca acattgcaaa aaattaagtt    720
cttgggtctt attaatgaag tatttaggta acgctactgc tatttttttt ttaccagacg    780
aaggtaagct tcaacattta gagaatgagt tgactcatga cattattact aaattttttag   840 agaacgagga tcgtcgtagc gcttctctgc acctgccaaa gttaagtatc accggtactt    900
acgacttaaa atctgtttta ggccagttag gtattaccaa agtttttttct aacggtgccg    960
```

```
atttgagtgg tgttactgaa gaagctccat taaaattgag taaagctgtt cacaaagccg   1020
tcttaactat tgatgaaaag ggtaccgagg ccgccggcgc tatgttcctg gaagctattc   1080
caatgagcat tccaccagaa gttaaattta ataaaccatt cgttttctg atgatcgagc    1140 agaacactaa aagcccattg tttatgggta aggttgtcaa cccaactcag aagatgtgca   1200
cgtgtgtccc accccaccca cagacggcct tctgcaattc cgacctcgtc atcagggcca   1260
agttcgtggg gacaccagaa gtcaaccaga ccaccttata ccagcgttat gagatcaaga   1320
tgaccaagat gtataaaggg ttccaagcct taggggatgc cgctgacatc cggttcgtct   1380
acacccccgc catggagagt gtctgcggat acttccacag gtcccacaac cgcagcgagg   1440
agtttctcat tgctggaaaa ctgcaggatg gactcttgca catcactacc tgcagtttcg   1500
tggctccctg gaacagcctg agcttagctc agcgccgggg cttcaccaag acctacactg   1560
ttggctgtga ggaatgcaca gtgtttccct gtttatccat cccctgcaaa ctgcagagtg   1620
gcactcattg cttgtggacg gaccagctcc tccaaggctc tgaaaagggc ttccagtccc   1680
gtcaccttgc ctgcctgcct cgggagccag ggctgtgcac ctggcagtcc ctgcggtccc   1740
agatagccta gtcgac                                                  1756

<210> SEQ ID NO 18
<211> LENGTH: 580
<212> TYPE: PRT
<213> ORGANISM: Homo sapiens

<400> SEQUENCE: 18

Met Glu Asp Pro Gln Gly Asp Ala Ala Gln Lys Thr Asp Thr Ser His
  1               5                  10                  15

His Asp Gln Asp His Pro Thr Phe Asn Lys Ile Thr Pro Asn Leu Ala
                 20                  25                  30

Glu Phe Ala Phe Ser Leu Tyr Arg Gln Leu Ala His Gln Ser Asn Ser
             35                  40                  45

Thr Asn Ile Phe Phe Ser Pro Val Ser Ile Ala Thr Ala Phe Ala Met
         50                  55                  60

Leu Ser Leu Gly Thr Lys Ala Asp Thr His Asp Glu Ile Leu Glu Gly
 65                  70                  75                  80

Leu Asn Phe Asn Leu Thr Glu Ile Pro Glu Ala Gln Ile His Glu Gly
                 85                  90                  95

Phe Gln Glu Leu Leu Arg Thr Leu Asn Gln Pro Asp Ser Gln Leu Gln
            100                 105                 110

Leu Thr Thr Gly Asn Gly Leu Phe Leu Ser Glu Gly Leu Lys Leu Val
        115                 120                 125

Asp Lys Phe Leu Glu Asp Val Lys Lys Leu Tyr His Ser Glu Ala Phe
    130                 135                 140

Thr Val Asn Phe Gly Asp Thr Glu Glu Ala Lys Lys Gln Ile Asn Asp
145                 150                 155                 160

Tyr Val Glu Lys Gly Thr Gln Gly Lys Ile Val Asp Leu Val Lys Glu
                165                 170                 175

Leu Asp Arg Asp Thr Val Phe Ala Leu Val Asn Tyr Ile Phe Phe Lys
            180                 185                 190

Gly Lys Trp Glu Arg Pro Phe Glu Val Lys Asp Thr Glu Glu Glu Asp
        195                 200                 205

Phe His Val Asp Gln Val Thr Thr Val Lys Val Pro Met Met Lys Arg
    210                 215                 220

Leu Gly Met Phe Asn Ile Gln His Cys Lys Lys Leu Ser Ser Trp Val
```

```
            225                 230                 235                 240
Leu Leu Met Lys Tyr Leu Gly Asn Ala Thr Ala Ile Phe Phe Leu Pro
                245                 250                 255

Asp Glu Gly Lys Leu Gln His Leu Glu Asn Glu Leu Thr His Asp Ile
            260                 265                 270

Ile Thr Lys Phe Leu Glu Asn Glu Asp Arg Arg Ser Ala Ser Leu His
        275                 280                 285

Leu Pro Lys Leu Ser Ile Thr Gly Thr Tyr Asp Leu Lys Ser Val Leu
    290                 295                 300

Gly Gln Leu Gly Ile Thr Lys Val Phe Ser Asn Gly Ala Asp Leu Ser
305                 310                 315                 320

Gly Val Thr Glu Glu Ala Pro Leu Lys Leu Ser Lys Ala Val His Lys
                325                 330                 335

Ala Val Leu Thr Ile Asp Glu Lys Gly Thr Glu Ala Ala Gly Ala Met
            340                 345                 350

Phe Leu Glu Ala Ile Pro Met Ser Ile Pro Pro Glu Val Lys Phe Asn
        355                 360                 365

Lys Pro Phe Val Phe Leu Met Ile Glu Gln Asn Thr Lys Ser Pro Leu
    370                 375                 380

Phe Met Gly Lys Val Val Asn Pro Thr Gln Lys Met Cys Thr Cys Val
385                 390                 395                 400

Pro Pro His Pro Gln Thr Ala Phe Cys Asn Ser Asp Leu Val Ile Arg
                405                 410                 415

Ala Lys Phe Val Gly Thr Pro Glu Val Asn Gln Thr Thr Leu Tyr Gln
            420                 425                 430

Arg Tyr Glu Ile Lys Met Thr Lys Met Tyr Lys Gly Phe Gln Ala Leu
        435                 440                 445

Gly Asp Ala Ala Asp Ile Arg Phe Val Tyr Thr Pro Ala Met Glu Ser
    450                 455                 460

Val Cys Gly Tyr Phe His Arg Ser His Asn Arg Ser Glu Glu Phe Leu
465                 470                 475                 480

Ile Ala Gly Lys Leu Gln Asp Gly Leu Leu His Ile Thr Thr Cys Ser
                485                 490                 495

Phe Val Ala Pro Trp Asn Ser Leu Ser Leu Ala Gln Arg Arg Gly Phe
            500                 505                 510

Thr Lys Thr Tyr Thr Val Gly Cys Glu Glu Cys Thr Val Phe Pro Cys
        515                 520                 525

Leu Ser Ile Pro Cys Lys Leu Gln Ser Gly Thr His Cys Leu Trp Thr
    530                 535                 540

Asp Gln Leu Leu Gln Gly Ser Glu Lys Gly Phe Gln Ser Arg His Leu
545                 550                 555                 560

Ala Cys Leu Pro Arg Glu Pro Gly Leu Cys Thr Trp Gln Ser Leu Arg
                565                 570                 575

Ser Gln Ile Ala
            580

<210> SEQ ID NO 19
<211> LENGTH: 1582
<212> TYPE: DNA
<213> ORGANISM: Homo sapiens

<400> SEQUENCE: 19
tctagaccat ggaagaccct caaggcgacg ccgctcaaaa aaccgacacc agtcatcacg      60
accaagacca tccgactttt aataaaatta ctccaaattt agccgaattt gcttttcctt    120
```

```
tgtatagaca attagctcat caaagtaatt ctactaacat ttttttagt cctgtttcta      180
ttgccactgc tttcgccatg ttgagtttag gtactaaagc cgatacccat gacgagattt      240
tagaaggttt aaactttaat ttgaccgaaa tcccagaagc ccaaattcac gagggttttc      300
aagagttgtt gagaactttg aatcaacctg attctcaatt gcaattaact actggtaacg      360
gtttattttt gtctgaaggt ttaaaattgg ttgacaaatt cctagaagac gtcaagaaac      420
tatatcatag tgaggctttt accgttaatt tggtgatac tgaggaagct aaaaagcaaa      480
ttaatgatta tgttgagaaa ggcacccagg gtaagatcgt tgacctagtt aaagaattag      540
atcgtgatac cgtcttcgca ctagttaact atatttttt caagggtaag tgggaacgtc      600
ctttcgaggt taaagatact gaagaggaag attttcatgt tgatcaagtt actactgtca      660
aagttccaat gatgaaaaga ctgggtatgt tcaatattca acattgcaaa aaattaagtt      720
cttgggtctt attaatgaag tatttaggta acgctactgc tattttttt ttaccagacg      780
aaggtaagct tcaacattta gagaatgagt tgactcatga cattattact aaattttag      840
agaacgagga tcgtcgtagc gcttctctgc acctgccaaa gttaagtatc accggtactt      900
acgacttaaa atctgtttta ggccagttag gtattaccaa agttttttct aacggtgccg      960
atttgagtgg tgttactgaa gaagctccat taaaattgag taaagctgtt cacaaagccg     1020
tcttaactat tgatgaaaag ggtaccgagg ccgccggcgc tatgttcctg gaagctattc     1080
caatgagcat tccaccagaa gttaaattta ataaaccatt cgtttttctg atgatcgagc     1140
agaacactaa aagcccattg tttatgggta aggttgtcaa cccaactcag aagatgtgca     1200
cgtgtgtccc accccaccca cagacggcct tctgcaattc cgacctcgtc atcagggcca     1260
agttcgtggg gacaccagaa gtcaaccaga ccaccttata ccagcgttat gagatcaaga     1320
tgaccaagat gtataaaggg ttccaagcct taggggatgc cgctgacatc cggttcgtct     1380
acacccccgc catggagagt gtctgcggat acttccacag gtcccacaac cgcagcgagg     1440
agtttctcat tgctggaaaa ctgcaggatg gactcttgca catcactacc tgcagtttcg     1500
tggctccctg gaacagcctg agcttagctc agcgccgggg cttcaccaag acctacactg     1560
ttggctgtga ggaatagtcg ac                                               1582
```

<210> SEQ ID NO 20
<211> LENGTH: 522
<212> TYPE: PRT
<213> ORGANISM: Homo sapiens

<400> SEQUENCE: 20

Met Glu Asp Pro Gln Gly Asp Ala Ala Gln Lys Thr Asp Thr Ser His
1               5                   10                  15

His Asp Gln Asp His Pro Thr Phe Asn Lys Ile Thr Pro Asn Leu Ala
            20                  25                  30

Glu Phe Ala Phe Ser Leu Tyr Arg Gln Leu Ala His Gln Ser Asn Ser
        35                  40                  45

Thr Asn Ile Phe Phe Ser Pro Val Ser Ile Ala Thr Ala Phe Ala Met
    50                  55                  60

Leu Ser Leu Gly Thr Lys Ala Asp Thr His Asp Glu Ile Leu Glu Gly
65                  70                  75                  80

Leu Asn Phe Asn Leu Thr Glu Ile Pro Glu Ala Gln Ile His Glu Gly
                85                  90                  95

Phe Gln Glu Leu Leu Arg Thr Leu Asn Gln Pro Asp Ser Gln Leu Gln
            100                 105                 110

Leu Thr Thr Gly Asn Gly Leu Phe Leu Ser Glu Gly Leu Lys Leu Val

```
                115                 120                 125
Asp Lys Phe Leu Glu Asp Val Lys Lys Leu Tyr His Ser Glu Ala Phe
130                 135                 140

Thr Val Asn Phe Gly Asp Thr Glu Ala Lys Lys Gln Ile Asn Asp
145                 150                 155                 160

Tyr Val Glu Lys Gly Thr Gln Gly Lys Ile Val Asp Leu Val Lys Glu
                165                 170                 175

Leu Asp Arg Asp Thr Val Phe Ala Leu Val Asn Tyr Ile Phe Phe Lys
            180                 185                 190

Gly Lys Trp Glu Arg Pro Phe Glu Val Lys Asp Thr Glu Glu Glu Asp
        195                 200                 205

Phe His Val Asp Gln Val Thr Thr Val Lys Val Pro Met Met Lys Arg
    210                 215                 220

Leu Gly Met Phe Asn Ile Gln His Cys Lys Lys Leu Ser Ser Trp Val
225                 230                 235                 240

Leu Leu Met Lys Tyr Leu Gly Asn Ala Thr Ala Ile Phe Phe Leu Pro
                245                 250                 255

Asp Glu Gly Lys Leu Gln His Leu Glu Asn Glu Leu Thr His Asp Ile
            260                 265                 270

Ile Thr Lys Phe Leu Glu Asn Glu Asp Arg Arg Ser Ala Ser Leu His
        275                 280                 285

Leu Pro Lys Leu Ser Ile Thr Gly Thr Tyr Asp Leu Lys Ser Val Leu
    290                 295                 300

Gly Gln Leu Gly Ile Thr Lys Val Phe Ser Asn Gly Ala Asp Leu Ser
305                 310                 315                 320

Gly Val Thr Glu Glu Ala Pro Leu Lys Leu Ser Lys Ala Val His Lys
                325                 330                 335

Ala Val Leu Thr Ile Asp Glu Lys Gly Thr Glu Ala Ala Gly Ala Met
            340                 345                 350

Phe Leu Glu Ala Ile Pro Met Ser Ile Pro Pro Glu Val Lys Phe Asn
        355                 360                 365

Lys Pro Phe Val Phe Leu Met Ile Glu Gln Asn Thr Lys Ser Pro Leu
    370                 375                 380

Phe Met Gly Lys Val Val Asn Pro Thr Gln Lys Met Cys Thr Cys Val
385                 390                 395                 400

Pro Pro His Pro Gln Thr Ala Phe Cys Asn Ser Asp Leu Val Ile Arg
                405                 410                 415

Ala Lys Phe Val Gly Thr Pro Glu Val Asn Gln Thr Thr Leu Tyr Gln
            420                 425                 430

Arg Tyr Glu Ile Lys Met Thr Lys Met Tyr Lys Gly Phe Gln Ala Leu
        435                 440                 445

Gly Asp Ala Ala Asp Ile Arg Phe Val Tyr Thr Pro Ala Met Glu Ser
    450                 455                 460

Val Cys Gly Tyr Phe His Arg Ser His Asn Arg Ser Glu Glu Phe Leu
465                 470                 475                 480

Ile Ala Gly Lys Leu Gln Asp Gly Leu Leu His Ile Thr Thr Cys Ser
                485                 490                 495

Phe Val Ala Pro Trp Asn Ser Leu Ser Leu Ala Gln Arg Arg Gly Phe
            500                 505                 510

Thr Lys Thr Tyr Thr Val Gly Cys Glu Glu
        515                 520

<210> SEQ ID NO 21
<211> LENGTH: 397
```

<212> TYPE: DNA
<213> ORGANISM: Homo sapiens

<400> SEQUENCE: 21
tctagaccat gtgcacctgt gtcccacccc acccacagac ggccttctgc aattccgacc 60
tcgtcatcag ggccaagttc gtggggacac cagaagtcaa ccagaccacc ttataccagc 120
gttatgagat caagatgacc aagatgtata aagggttcca agccttaggg gatgccgctg 180
acatccggtt cgtctacacc cccgccatgg agagtgtctg cggatacttc cacaggtccc 240
acaaccgcag cgaggagttt ctcattgctg gaaaactgca ggatggactc ttgcacatca 300
ctacctgcag tttcgtggct ccctggaaca gcctgagctt agctcagcgc cggggcttca 360
ccaagacgta tactgttggc tgtgaggaat agtcgac 397

<210> SEQ ID NO 22
<211> LENGTH: 127
<212> TYPE: PRT
<213> ORGANISM: Homo sapiens

<400> SEQUENCE: 22

```
Met Cys Thr Cys Val Pro Pro His Pro Gln Thr Ala Phe Cys Asn Ser
 1               5                  10                  15

Asp Leu Val Ile Arg Ala Lys Phe Val Gly Thr Pro Glu Val Asn Gln
            20                  25                  30

Thr Thr Leu Tyr Gln Arg Tyr Glu Ile Lys Met Thr Lys Met Tyr Lys
        35                  40                  45

Gly Phe Gln Ala Leu Gly Asp Ala Ala Asp Ile Arg Phe Val Tyr Thr
    50                  55                  60

Pro Ala Met Glu Ser Val Cys Gly Tyr Phe His Arg Ser His Asn Arg
65                  70                  75                  80

Ser Glu Glu Phe Leu Ile Ala Gly Lys Leu Gln Asp Gly Leu Leu His
                85                  90                  95

Ile Thr Thr Cys Ser Phe Val Ala Pro Trp Asn Ser Leu Ser Leu Ala
            100                 105                 110

Gln Arg Arg Gly Phe Thr Lys Thr Tyr Thr Val Gly Cys Glu Glu
        115                 120                 125
```

<210> SEQ ID NO 23
<211> LENGTH: 400
<212> TYPE: DNA
<213> ORGANISM: Homo sapiens

<400> SEQUENCE: 23
tctagaccat gtgcacctgt gtcccacccc acccacagac ggccttctgc aattccgacc 60
tcgtcatcag ggccaagttc gtggggacac cagaagtcaa ccagaccacc ttataccagc 120
gttatgagat caagatgacc aagatgtata aagggttcca agccttaggg gatgccgctg 180
acatccggtt cgtctacacc cccgccatgg agagtgtctg cggatacttc cacaggtccc 240
acaaccgcag cgaggagttt ctcattgctg gaaaactgca ggatggactc ttgcacatca 300
ctacctgcag tttcgtggct ccctggaaca gcctgagctt agctcagcgc cggggcttca 360
ccaagacgta tactgttggc tgtgaggaat gctagtcgac 400

<210> SEQ ID NO 24
<211> LENGTH: 128
<212> TYPE: PRT
<213> ORGANISM: Homo sapiens

<400> SEQUENCE: 24

Met Cys Thr Cys Val Pro Pro His Pro Gln Thr Ala Phe Cys Asn Ser
1               5                   10                  15

Asp Leu Val Ile Arg Ala Lys Phe Val Gly Thr Pro Glu Val Asn Gln
            20                  25                  30

Thr Thr Leu Tyr Gln Arg Tyr Glu Ile Lys Met Thr Lys Met Tyr Lys
        35                  40                  45

Gly Phe Gln Ala Leu Gly Asp Ala Ala Asp Ile Arg Phe Val Tyr Thr
    50                  55                  60

Pro Ala Met Glu Ser Val Cys Gly Tyr Phe His Arg Ser His Asn Arg
65              70                  75                  80

Ser Glu Glu Phe Leu Ile Ala Gly Lys Leu Gln Asp Gly Leu Leu His
                85                  90                  95

Ile Thr Cys Ser Phe Val Ala Pro Trp Asn Ser Leu Ser Leu Ala
            100                 105                 110

Gln Arg Arg Gly Phe Thr Lys Thr Tyr Thr Val Gly Cys Glu Glu Cys
        115                 120                 125

<210> SEQ ID NO 25
<211> LENGTH: 72
<212> TYPE: DNA
<213> ORGANISM: Homo sapiens

<400> SEQUENCE: 25
atgccgtctt ctgtctcgtg gggcatcctc ctgctggcag gcctgtgctg cctggtccct    60
gtctccctgg ct                                                        72

<210> SEQ ID NO 26
<211> LENGTH: 24
<212> TYPE: PRT
<213> ORGANISM: Homo sapiens

<400> SEQUENCE: 26

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 27
<211> LENGTH: 75
<212> TYPE: DNA
<213> ORGANISM: Homo sapiens

<400> SEQUENCE: 27
atgaagtcca gcggcctctt ccccttcctg gtgctgcttg ccctgggaac tctggcacct    60
tgggctgtgg aaggc                                                     75

<210> SEQ ID NO 28
<211> LENGTH: 25
<212> TYPE: PRT
<213> ORGANISM: Homo sapiens

<400> SEQUENCE: 28

Met Lys Ser Ser Gly Leu Phe Pro Phe Leu Val Leu Leu Ala Leu Gly
1               5                   10                  15

Thr Leu Ala Pro Trp Ala Val Glu Gly
            20                  25

<210> SEQ ID NO 29
<211> LENGTH: 69

```
<212> TYPE: DNA
<213> ORGANISM: Homo sapiens

<400> SEQUENCE: 29 atggcccct ttgagcccct ggcttctggc atcctgttgt tgctgtggct gatagccccc    60
agcagggcc                                                            69

<210> SEQ ID NO 30
<211> LENGTH: 23
<212> TYPE: PRT
<213> ORGANISM: Homo sapiens

<400> SEQUENCE: 30

Met Ala Pro Phe Glu Pro Leu Ala Ser Gly Ile Leu Leu Leu Trp
 1               5                  10                  15

Leu Ile Ala Pro Ser Arg Ala
             20

<210> SEQ ID NO 31
<211> LENGTH: 269
<212> TYPE: DNA
<213> ORGANISM: Homo sapiens

<400> SEQUENCE: 31
atgagatttc cttcaatttt tactgcagtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc catttccaa cagcacaaat    180 aacgggttat tgtttataaa tactactatt gccagcattg ctgctaaaga agaaggggta   240
tctctagata aaagagaggc tgaagcttg                                     269

<210> SEQ ID NO 32
<211> LENGTH: 89
<212> TYPE: PRT
<213> ORGANISM: Homo sapiens

<400> SEQUENCE: 32

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                 20                  25                  30

Ile Pro Ala Glu Ala Val Ile Gly Tyr Ser Asp Leu Glu Gly Asp Phe
             35                  40                  45

Asp Val Ala Val Leu Pro Phe Ser Asn Ser Thr Asn Asn Gly Leu Leu
 50                  55                  60

Phe Ile Asn Thr Thr Ile Ala Ser Ile Ala Ala Lys Glu Glu Gly Val
 65                  70                  75                  80

Ser Leu Asp Lys Arg Glu Ala Glu Ala
                 85

<210> SEQ ID NO 33
<211> LENGTH: 4
<212> TYPE: PRT
<213> ORGANISM: Artificial sequence
<220> FEATURE:
<223> OTHER INFORMATION: Synthetic construct

<400> SEQUENCE: 33

Ala Ala Pro Val
 1
```